(12) United States Patent
Cunningham et al.

(10) Patent No.: US 6,262,024 B1
(45) Date of Patent: Jul. 17, 2001

(54) NEURON REGULATORY FACTOR FOR PROMOTING NEURON SURVIVAL

(75) Inventors: Timothy J. Cunningham, Fort Washington; Forrest Haun, Wyncote, both of PA (US); Kathie L. Eagleson, Somerville, NJ (US); Pat R. Levitt, Wyncote; Sarah E. Kennedy, Ambler, both of PA (US)

(73) Assignee: Philadelphia, Health and Education Corporation, Philadelphia, PA (US)

( * ) Notice: Subject to any disclaimer, the term of this patent is extended or adjusted under 35 U.S.C. 154(b) by 0 days.

(21) Appl. No.: 08/936,477

(22) Filed: Sep. 18, 1997

Related U.S. Application Data

(63) Continuation-in-part of application No. 08/609,050, filed as application No. PCT/US94/10051 on Aug. 31, 1994, now abandoned, which is a continuation-in-part of application No. 08/115,748, filed on Sep. 1, 1993, now abandoned.

(51) Int. Cl.[7] .................. C07K 14/475; A61K 38/18
(52) U.S. Cl. .................. 514/12; 530/399; 530/350; 530/324; 435/69.4
(58) Field of Search .................. 530/350, 399, 530/324; 514/12; 435/69.4

(56) References Cited

U.S. PATENT DOCUMENTS 5,215,969    6/1993    Springer et al. .................. 514/21

OTHER PUBLICATIONS

Por et al. J. Biol. Chem. 259 : 6526–6533, 1984.*
Rudinger, In "Peptide Harmones" (Ed. J.A. Parsons) University Park Press, Baltimore, pp. 1–7, 1976.*
Barde et al. (1982), EMBO J., 1: 549–53.
Chany (1987), J. Interferon Res. 7:569–574.
Chany–Fournier, et al. (1978), Proc. Natl. Acad. Sci. 75:2333–2337.
Chany–Fournier et al. (1990), J. Cell. Physiol. 145:173–180.
Eagleson et al. (1990), Experimental Neurology, 110: 284–90.
Eagleson et al. (1992), Experimental Neurology, 116: 156–62.
Furukawa et al. (1995), Exp. Neurol. 133: 153–163.
Globus et al. (1991), J. Neurochem., 57: 470–478.
Guilian et al. (1993), Glia, 7:102–110.
Leibrock et al. (1989), Nature, 341: 149–52.
Mayer et al. (1989), Nature, 338:425–427.
Naharro et al. (1984), Science, 223: 63–66.
Rosenmund & Westbrook (1993), Neuron, 10: 805–814.
Springer, J.E. (1991), Drug News and Perspectives, 4: 394–99.
Thanos and Mey (1995) J. Neurosci. 15(2):1057–1079.
Yoshizawa, et al. (1992), J. Immunol. 148: 3110–3116.
Zeng et al. (1994), Biochem. Biophys. Res. Comm. 200:89–98.
Zeng et al. (1993), Arch. Biochem. Biophys. 303:74–80.
Zeng, et al. (1994), Biol. Chem. Hoppe–Seyler 375:393–399.
Eagleson, et al. (1990), Soc. for Neurosci. Abstracts 16:995 (412.16).
Eagleson, et al. (1992), Soc. for Neurosci. Abstracts 18:1478 (621.17).

\* cited by examiner

*Primary Examiner*—Gary L. Kunz
*Assistant Examiner*—Robert C. Hayes
(74) *Attorney, Agent, or Firm*—Dann, Dorfman, Herrell and Skillman

(57) ABSTRACT

A neuron regulatory factor (NRF), derived from cells of the central nervous system, is provided. A cytoprotective peptide (CPP) component of NRF is also provided, as are methods of using NRF or its CPP component. NRF comprises a large polypeptide or complex of polypeptides that is distinct from several other known neurotrophic or neuron regulatory factors. The CPP component of NRF is an acidic protein or protein complex whose amino acid sequence is unique among known protein sequences. Both NRF and its CPP component are capable of promoting survival and neurite outgrowth of cultured neurons in vitro, and preventing neuron degeneration and promoting neuron survival in vivo. The CPP component of NRF also exhibits a cytoprotective effect on non-neuronal cells.

7 Claims, 18 Drawing Sheets

ELUTED GEL BAND
(Purification of peptide from $H_2O_2$ treated cell lines)

SYNTHETIC PEPTIDE

NEURON REGULATORY FACTOR FOR PROMOTING NEURON SURVIVAL

This application is a continuation-in-part of PCT Application Serial No. 08/609,050 filed Feb. 29, 1996 now abandoned, which claims priority from PCT/US94/10051, filed Aug. 31, 1994 and designating the United States of America, which itself is a continuation-in-part of U.S. application Ser. No. 08/115,748, filed Sep. 1, 1993, now abandoned. These applications are incorporated herein by reference.

Pursuant to 35 U.S.C. §202(c), it is hereby acknowledged that the U.S. Government has certain rights in the invention described herein, which was made in part with funds from the National Institutes of Health, NS16487.

FIELD OF THE INVENTION

The present invention relates to a composition of matter comprising a neuron regulatory factor or a component thereof, for promoting neurite outgrowth and enhancing survival of both neuronal and non-neuronal cells, to a pharmaceutical preparation containing the neuron regulatory factor or component thereof, and to its use in the treatment of damaged neurons or non-neuronal cells.

BACKGROUND OF THE INVENTION

Neurotrophic factors are considered to be vital for normal development of the nervous system. During development, neuronal target structures produce limited amounts of specific neurotrophic factors necessary for both the survival and differentiation of neurons projecting into the structures. The same factors have been found to be involved in the survival and/or maintenance of mature neurons.

A neurotrophic factor is defined as a substance capable of increasing and/or maintaining survival of a neuron population, and possibly affecting outgrowth of neurites (neuron processes) and certain other metabolic activities of a neuron. Neurotrophic factors are generally described as soluble molecules synthesized in the peripheral targets of neurons and transported to their cell bodies, where they exert their effects.

Studies with isolated neurotrophic factors have shown that exogenously added neurotrophic factors can exert their neurotrophic effects upon cultured neurons in vitro, or by administration to damaged or degenerated neurons in vivo. For this reason, various neurotrophic factors have received great attention as potential therapeutic agents for treatment of degenerative diseases of the central nervous system, as well as traumatic damage to the CNS. For example, nerve growth factor (NGF) has been shown to increase the survival, function and regeneration of cholinergic neurons in the basal forebrain. Degeneration of this population of cholinergic neurons has been associated with patients having Alzheimer's disease, and could be the primary neuronal defect responsible for the loss of cognitive function associated with Alzheimer's disease. NGF has been found to be synthesized and released from the target areas of these cholinergic neurons in the hippocampus and neurocortex, both areas of the brain associated with learning and memory. See Springer, J. E., Drug News and Perspectives, 4: 394–99 (1991). As another example, a dopaminergic neurotrophic factor (DNTF) has been purified and characterized, and found to promote survival and neurite outgrowth of dopaminergic neurons of the substantia nigra. DNTF is considered a potentially valuable therapeutic agent for the treatment of Parkinson's disease which involves degeneration of dopaminergic motor neurons of the central nervous system (U.S. Pat. No. 5,215,969 to Springer et al., 1993).

It can be seen from the foregoing examples that neurotrophic factors are a valuable source of therapeutic agents for the treatment of neuron damage and neurodegenerative disease. However, the development of such factors as therapeutic agents can be problematic. For example, it is difficult to determine the specificity of an endogenous neurotrophic agent, i.e., whether different factors exist for different nervous system pathways, and which neuron populations in those pathways are affected by a factor. In fact, many identified neurotrophic agents have been shown to have a wide range of biological functions, acting on both central and peripheral neurons, as well as non-neuronal cells in vitro (e.g., polypeptide growth factors and ciliary neurotrophic factor, CNTF). In the central nervous system, with its complex interconnections and heterogeneous neuron types, it is difficult to determine which neurotrophic factors are effective on a particular neuronal population. This difficulty is further exacerbated by the fact that many of the neurotrophic factors that have been characterized have been found to be closely related to one another. For example, it is now known that NGF possesses amino acid sequence homology to brain-derived neurotrophic factor (BNDF), a protein with similar, but not identical, in vitro properties as NGF (Barde et al., EMBO J., 1: 549–53, 1982; Leibrock et al., Nature, 341: 149–52, 1989). In fact, NGF, BNDF and the neurotrophin (NT) series have been classified as members of a superfamily of neurotrophic factors (NGF superfamily). Because of their similarity in amino acid sequence (and hence nucleotide sequences encoding the factor), it has been difficult to develop nucleic acid or antibody probes that are specific for a particular member of the family. The lack of a specific means for identifying a particular neurotrophic factor has hindered the elucidation of particular neuronal populations affected by a specific factor.

An additional obstacle to developing neurotrophic factors as therapeutic agents for treatment of damaged neurons is that few in vivo models exist to study the survival-promoting activity of these factors in the central nervous system. In order to develop a neurotrophic factor as an effective therapeutic agent for the treatment of neuron degeneration, it is important to be able to determine where in the central nervous system the neurotrophic factor operates, whether the treatment with exogenous neurotrophic factor is effective, and the concentration of neurotrophic factor effective for imparting a therapeutic effect. Such an objective would best be accomplished with a neurotrophic factor that is identifiable and distinct from other factors, that is capable of exerting an effect on many different neuron populations, and for which in vivo models are available to test the efficacy of the neurotrophic factor on a specific neuron population.

SUMMARY OF THE INVENTION

In accordance with one aspect of the present invention, there is provided a purified neuron regulatory factor for supporting survival of neurons. This factor is referred to as "neuron regulatory factor" ("NRF") because it possesses a variety of neuroprotective activities, including the neuron growth and survival-promoting activities traditionally attributed to neurotrophic factors. NRF comprises a complex of polypeptides of molecular weight between about 2,500 and 250,000 Da as determined by SDS-polyacrylamide gel electrophoresis under non-reducing conditions, and exhibits a neurotrophic and neuron-regulatory effect on cells of the nervous system in vitro and in vivo.

As described in the Examples set forth below, NRF can be purified from a variety of sources. The complex has been purified from conditioned medium from embryonic primordia comprising the geniculocortical pathway. NRF from conditioned medium is sometimes referred to herein as NRFcm. Following isolation from tissue culture media, the complex is subjected to HPLC. Following this purification step, the protein may be further purified over an immunoaffinity column. Electrophoretic resolution of NRF so purified reveals bands migrating at approximately 55, 110 and 200 kDa. It is possible that the higher molecular weight polypeptide is comprised of multimers of the lower molecular weight polypeptides.

NRF has also been purified from homogenates of rat cerebral cortex tissue. The purification of NRF from cytosolic fractions of cerebral cortex tissue is described in Example 7. Like the NRF purified from conditioned medium, resolution of NRF from the cerebral cortex on polyacrylamide gels reveals a protein migrating at approximately 200 kDa.

Example 9 sets forth methods utilized to purify NRF from human retinoblastoma cells. This protein, sometimes referred to herein as NRFrb, also migrates at approximately 200 kd on polyacrylamide gels.

In another embodiment of the invention, NRF is further purified over an immunoaffinity column specific for cytosolic or secreted actin, followed by acid separation on a superose 12 column. NRF so purified is referred to herein as NRFSCI for neuron regulatory factor subcomponent 1. Resolution of NRFSCI on polyacrylamide gels reveals bands migrating at 3–8, 14–21, 30 and 66–69 kDa. The 3–8 and 14–21 bands have been eluted from the gel and tested in vitro and in vivo for activity. In early studies, this factor, NRFSCI, has been referred to as the "cytoprotective protein" (CPP) because it possesses a general cytoprotective activity on different neuronal and non-neuronal populations in vitro and in vivo. A partial amino acid sequence analysis of NRFSCI reveals no significant homologies with any other publicly-available amino acid sequences.

NRF comprises at least one amino acid sequence that is substantially identical to a sequence found in actin. When comparatively referring to amino acid sequences herein, the term "substantially identical to" or "substantially the same as" is intended to refer to conservative substitutions or natural mutations that occur in nature. As such alterations do not materially affect the overall structure or activity of the protein containing the sequence, such sequences are contemplated to be within the scope of the invention.

As mentioned above, also present in NRFSCI is a small (approximately 3–8 kD), highly acidic protein. This smaller fragment is closely associated with some globular proteins such as albumin and IgG. The peptide also specifically binds sialidated Ig sequences on the cell surface and may also interact with actin molecules.

In another embodiment of the invention, a synthetic NRFSCI peptide has been synthesized having the sequence of Sequence I.D. No. 3. This synthetic NRF peptide exhibits similar neuronal growth promoting effects on HN cells as those observed using native NRFSCI 3–8 kd fragment eluted from gels. The synthetic peptide also migrates with native NRFSCI, 3–8 kDa peptide and exhibits a similar staining pattern.

NRF and its subcomponents are capable of increasing the survival and neurite outgrowth of cultured neurons in vitro, and are further capable of increasing the survival of neurons of neonatal and adult mammals in vivo, when such neurons are exposed to a pre-determined concentration of the neuron regulatory factor. NRF is capable of exerting its neurotrophic effect on a variety of neuron populations, in a concentration-dependent manner. NRF is capable of preventing nerve cell degeneration and stimulating nerve axon reorganization after damage to the central nervous system. As an actin-associated regulatory protein, NRF is further characterized by its association with neurotransmitter receptor/ion channel macromolecular complexes of cell membranes and its regulatory effect on such complexes.

In accordance with another aspect of this invention, there is provided a purified neuron regulatory factor, or NRFSCI component thereof, for supporting survival of neurons, which is isolated from a mammalian central nervous system and is immunologically cross-reactive with an antibody raised against NRF or NRFSCI from rat. The neuron regulatory factor, and particularly its NRFSCI component, are capable of increasing survival and neurite outgrowth of cultured neurons in vitro, and of increasing survival of neurons of neonatal and adult mammals in vivo, upon exposure of those neurons to a pre-determinded concentration of the neuron regulatory factor or the NRFSCI component. NRFSCI is also effective on non-neuronal cells, such as muscle.

Another object of the invention is the production of NRF specific probes for isolation of DNA molecules encoding the neuron regulatory factor of the invention. The probes provided herein facilitate the cloning of a cDNA molecule encoding NRFSCI. Isolation of a cDNA clone then provides suitable probes for the isolation of the gene encoding the protein from a genomic library.

In accordance with a further aspect of the present invention, there is provided a pharmaceutical preparation for the treatment of cell degeneration, specifically neuron degeneration in the central nervous system, which comprises, as the active agent, the aforementioned NRF, or its subcomponents, in an amount sufficient to increase the survival and function of damaged or degenerating cells in a multiplicity of locations in the body and, possibly, to cause regeneration of damaged neurons.

In accordance with yet another aspect of the present invention, there is provided a method for treating patients having damage to a particular tissue, such as tissue of the central nervous system, which comprises administering to such patients a pharmaceutical preparation containing the above-described NRF, components thereof, in a form that allows the active ingredients of the pharmaceutical preparation to reach the location of the damage. The pharmaceutical preparation may be administered, for example, in liquid form, or it may be immobilized in a solid matrix and implanted into the central nervous system, at the location of neuron damage.

The present invention represents a potentially significant advance in the treatment of neurodegenerative disorders and neuron damage resulting from a trauma, stroke and the like. The NRF of the present invention and its active subcomponents exert survival- and growth-promoting effects on a variety of different neuron and non-neuron populations when administered in appropriate concentrations. Moreover, biological assays are available for determining optimum concentrations of NRF or its subcomponents for treatment of selected neuron populations both in vitro and in vivo. In addition, NRF possesses several distinct physical properties, such as a large size in comparison with other neurotrophic factors, and is antigenically distinct from many other neurotrophic factors. NRFSCI is also physically distinct from other known proteins. The broad range of effectiveness, physical distinctiveness and availability of in vivo and in vitro assays are all notable advantages of NRF and its subcomponents for use in the treatment of neuron damage, neurodegenerative disease and other non-neural degenerative disease.

BRIEF DESCRIPTION OF THE DRAWINGS

The foregoing summary, as well as the following description of preferred embodiments of the present invention, will be better understood when read in conjunction with the appended drawings in which.

DETAILED DESCRIPTION OF THE INVENTION

Figure 1:
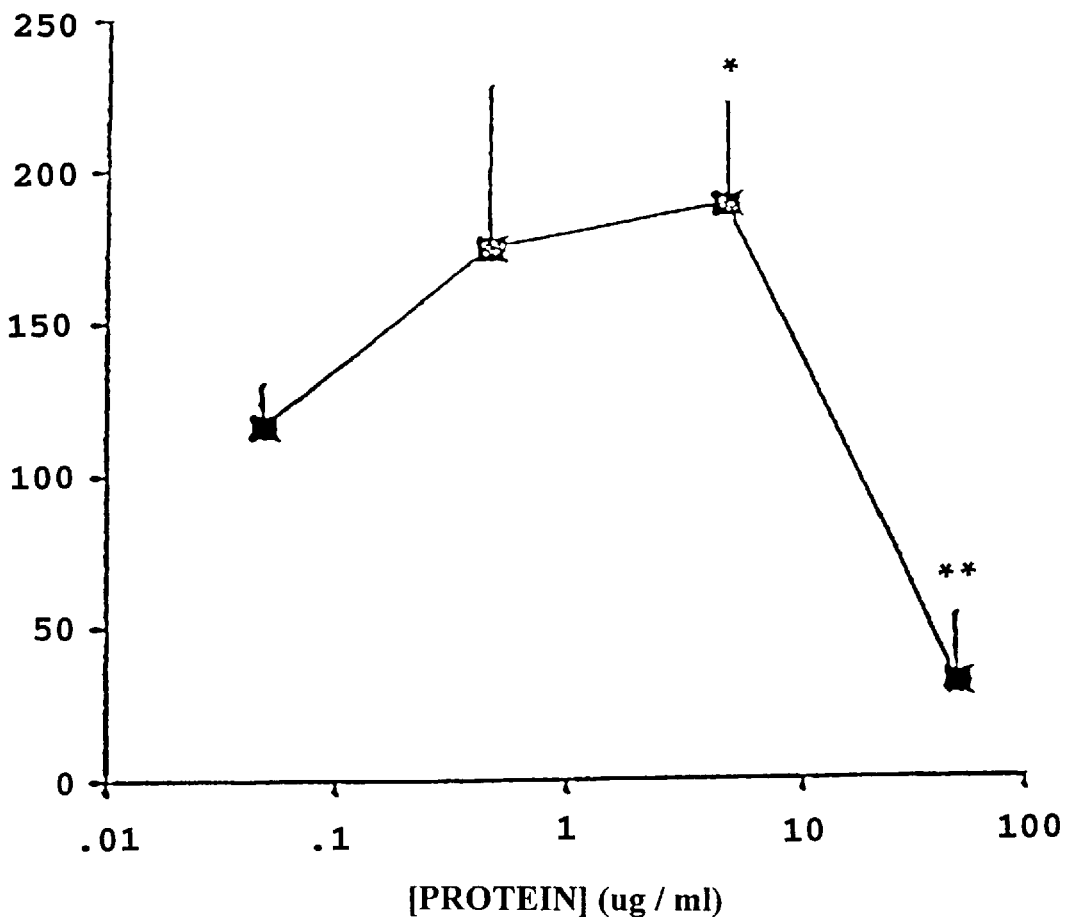
FIG. 1 is a graph of the effect of different concentrations of NRF affinity-purified from embryonic primordial-conditioned medium (NRFcm) on the survival of cultured E17 posterolateral thalamic neurons; x-axis represents protein concentration of CM affinity fraction containing NRFcm ($\mu$g/ml), y-axis represents the number of neurons at four different concentration treatments of NRFcm, expressed as a percentage of a control treatment (cells receiving no NRFcm); vertical lines=range between two independent experimental groups; *=statistically significant value.

In accordance with the present invention, a unique neuron regulatory factor, NRF, has been isolated and purified. In addition, a subcomponent of NRF, NRFSCI has been further purified and characterized. Initially, NRF was isolated from culture medium conditioned by embryonic primordia of neurons of the geniculocortical pathway (hereinafter sometimes referred to as NRFcm). Such conditioned cultured medium had previously been shown capable of exerting a neurotrophic effect on central nervous system neurons in vitro and in vivo. Eagleson et al., Experimental Neurology, 116: 156–62 (1992); Eagleson et al., Experimental Neurology, 110: 284–90 (1990). However, it was heretofore unknown what factor or factors in the condition medium was responsible for the neurotrophic effect. In accordance with the present invention, it is now known that the neurotrophic effect of the aforementioned conditioned medium is attributable to a neuron regulatory factor, NRF, and more specifically, to a biologically active protein component of NRF, NRFSCI. NRF is now known to comprise a complex of polypeptides, the total molecular weight of which exceeds 150,000 Da and which includes active components, such as the NRFSCI and cytoskeletal components, such as actin. NRF (and/or its subcomponents) can be purified from conditioned medium of neuron primordia or cultured neural cells, or it may be obtained from the membrane or cytosolic fractions of adult neurons or cultured neural cell lines.

The NRF of the present invention possesses several unique physical and functional features that are of considerable advantage in the development as a therapeutic agent for treatment of neuron damage and neurodegenerative diseases. NRFSCI of NRF itself is a unique protein or complex of proteins, possessing cytoprotective activity in very low concentrations. The unique features of NRF and its subcomponents are described in the Detailed Description and the Examples set forth hereinbelow, wherein preferred methods of making and using NRF, and active subcomponents thereof and related materials are described.

I. Isolation and Purification of NRF and its Subcomponents

A. Purification of NRF from Embryonic Primordia Conditioned Medium

Neurotrophic factors are generally present only in small quantities in brain tissue and, until recently, have been difficult to isolate. However, one method that has proved very successful in obtaining comparatively large quantities of neurotrophic factors is to produce the factors from embryonic tissue primordia from which arises a specific population of neuronal cells comprising the target for the neurotrophic factor. NRF is one such neurotrophic factor; it is synthesized in cultured embryonic primordia of the structures in the visual nerve pathway, and is secreted from those primordia into the culture medium. Therefore, such cultures provide a convenient source for isolating relatively large quantities of NRF, sufficient for further purification by standard immunochemical and chromatographic methods.

NRFcm may be prepared from conditioned media containing embryonic primordia of structures forming direct connections in the visual parts of the brain. In a preferred embodiment, embryonic posterior diencephalon and posterior cortex pieces are dissected from an embryo, and co-cultured for five days together. The primordia secrete NRF into the culture medium, where it is collected and subjected to further purification. A detailed description of the preparation of conditioned medium containing NRFcm is set forth in Example 1.

In alternative embodiments, embryonic primordia destined to develop into other pathways where NRF is localized can be utilized to provide conditioned medium containing NRF. Potential targets for NRF activity are located by immunostaining of the normal adult brain, as described in detail in Example 5. Once a target location is identified in such a manner, embryonic primordia that develop to form those target areas may also be identified. For example, in an alternative preferred embodiment, the embryonic primordia leading to the development of the medial frontal cerebral cortex (area 8) may be utilized to produce conditioned medium containing NRF, as described above and in Example 1. The preparation of conditioned medium containing NRFcm, from any population of primordia that develops into a target neuronal pathway is contemplated in the present invention.

Once a conditioned medium containing NRFcm has been prepared, the neuron regulatory factor may be further purified and concentrated according to standard procedures. For example, as described in detail in Example 1, conditioned medium may be subjected to high performance liquid chromatography (HPLC) to separate various protein fractions, which may then be tested for neurotrophic activity using one of the assays described hereinbelow and in Examples 2–4 and 8. Active fractions may then be pooled and concentrated for use in a pharmaceutical preparation, or for use as an antigen to produce immunospecific antibodies to NRF.

Immunospecific anti-NRF antibodies are useful for affinity purification of NRF from a variety of sources, as described hereinbelow. Additionally, such antibodies are useful for localizing the sites of NRF production and accumulation in vivo, as well as identifying the isolated protein by Western blotting and other immunoblotting methods.

B. Purification of NRF from Homogenates of Cerebral Cortex Tissue

As described above, although NRF is a relatively large polypeptide or complex of polypeptides, it is secreted from the cells of embryonic primordia into the culture medium. Additionally, it has been discovered in accordance with the present invention that NRF accumulates in association with both the membranes and the cytosolic fractions of cerebral cortex homogenates, particularly in cortices of neonatal rats (birth to post-natal day 10), and can also be isolated from cultured human retinoblastoma cells. In a preferred embodiment of the present invention, NRF is purified by immunoprecipitation from such homogenates, using the aforementioned anti-NRF antibodies. Preparation of NRF from homogenates of cerebral cortex tissue, NRFcc, is described in greater detail in Examples 6 and 7. Preparation of NRF from cultured human retinoblastoma cells, NRFrb is described in greater detail in Example 9.

Example 7 describes a detailed purification of NRFcc from the cytosolic fraction of cerebral cortex homogenates. Surprisingly, SDS-polyacrylamide gel electrophoresis followed by Western blotting of the cerebral cortex cytosolic homogenates revealed the most prominent immunologically stained band at approximately 200–220 kDa rather than the 45–65 kDa band, which was most prominent in the conditioned medium described above. The cortical cytosolic homogenates were subjected to affinity purification with the 8G6 antibody, as described in detail in Example 7, then separated by HPLC on a Superose 12 sizing column. The 200 kDa protein eluted from this column well after the elution of smaller proteins was observed. This atypical elution profile could be due to hydrophobic interactions of the protein with the Superose 12 matrix, which retards the elution of the protein from the column. Alternatively, a highly charged protein component of NRF could cause interaction with the matrix, thereby retarding elution of the entire NRF complex. Silver staining of the HPLC fraction containing this peak revealed a prominent 200 kDa band. Biological testing of this fraction demonstrated that it is active in in vitro and in vivo assays, such as those described in Examples 2–4 and 8, and that the activity is approximately 10–20-fold greater than that observed for the affinity-purified fraction of NRF from embryonic primordia conditioned medium. Thus, neurons from the fraction of neonatal rat cerebral cortex are an excellent and preferred source for the isolation and purification of NRF.

C. Preparation of NRF from Cultured Human Retinoblastoma Cells

In another preferred embodiment of the invention, the human form of NRF may be isolated and purified from cultured human retinoblastoma cells, hereinafter NRFrb. Purification of a molecule having properties of NRF from the medium of Y9 human retinoblastoma cell lines is described in detail in Example 10. These cells were selected as a possible source of NRF from human because of the dense immunostaining observed with rat NRF in the synaptic layer of the neonatal rat retina. A 200 kDa retinoblastoma protein, which is weakly immunoreactive to the 8G6 antibody, is purified from serum-free medium by ultrafiltration, dialysis and repeated HPLC runs, as described in Example 10. The human protein also supports the survival of rat thalamic neurons in a concentration-dependent manner, as demonstrated by the in vitro assays described in Example 8 below. The identification of a human source of NRF, such as NRFrb, enables development of the human protein as a human therapeutic agent.

D. Preparation of NRFSCI from Cultured Cells or from the Cytosolic Fraction of Cerebral Cortex Homogenates From the foregoing discussion, it appears that NRF comprises several components, which may represent distinct polypeptides, or which may comprise one or more hybrid polypeptides. In either case, NRF contains at least one cytoskeletal component and at least one biologically active cytoprotective component, NRFSCI.

It has been further discovered in accordance with the present invention that NRFsubcomponent I, NRFSCI, of NRF may be purified according to a novel protocol, which is believed to succeed because of the highly acidic nature of NRFSCI. This protocol is described in detail in Example 10, and can be performed from diverse starting materials, including, for example, the soluble fraction of rat brain homogenates as described above, and medium condition by cell lines that have neural properties (e.g. hippocampal cell lines from mouse, or the human Y9 retinoblastoma cell line).

The isolation of NRFSCI involves affinity purification using anti-actin antibodies instead of the 8G6 antibodies described above (it should be noted in any event that the 8G6 antibodies most likely cross-react with a cytoskeletal component of NRF, such as an actin epitope). The actin affinity purified material is then subjected to HPLC on a Superose 12 (Pharmacia) sizing column using 50 mM HCl as the elution solution. This results in elution of a protein fraction essentially devoid of actin epitopes, which can later be eluted from the column with a strong base. The acid eluted protein fraction is referred to herein as NRFSCI, and possesses several unusual features, as described in greater detail below and in Example 10. NRFSCI could be a distinct polypeptide or is a polypeptide complex. Alternatively, it could be an acid-hydrolytic product of a larger polypeptide.

E. Preparation of NRF or NRFSCI by Recombinant DNA Techniques

NRF or its subcomponents can also be prepared from isolated and purified cDNAs or genes encoding the polypeptide(s). Such a cDNA or gene can be obtained by standard methods, i.e., by immunologically identifying clones from an appropriate cDNA or genomic library that expresses proteins comprising the factor. For example, a cDNA library may be prepared from messenger RNA isolated from the embryonic primordia that naturally express NRF or its subcomponents thereof. Methods for preparing cDNA libraries are well known in the art. An appropriate cDNA expression library may then be screened with the antibodies raised against one or more epitopes of the NRF or its specific components, such as NRFSCI. See, e.g., Huynh et al., *DNA Cloning: A Practical Approach*, Vol. 1, D. M. Glover, ed., pp 49–78 (1985) for general methods of screening a lambda gt11 expression library. Such screening is likely to result in obtaining both partial and full-length clones encoding one or more components of NRF. Such clones may be used directly for expression, or may be used to screen genomic libraries, according to standard methods. A NRFSCI$_{14-21}$ polypeptide has been partially sequenced. The amino acid sequence is set forth as Sequence I.D. No. 3. This information enables the synthesis of the specific oligonucleotide probes described in Example 13 which may be used to probe cDNA libraries to isolate clones encoding this component of NRF.

A cDNA or gene encoding NRF, or other components thereof can be maintained in any common cloning vector, such as a plasmid, and maintained in an appropriate host cell, such as *E. coli*. Such cloning vectors can preferably also contain a bacteriophage transcription promoter, such as SP6, T7, or T3, inserted in the vector upstream from a DNA molecule encoding the selected protein. Such in vitro transcription vectors are commonly available (e.g., from Promega Biotech, Inc., Madison, Wis.). In vitro transcription of the DNA may then be carried out by, e.g., an SP6 RNA polymerase, using standard methods. Kits for performing in vitro transcription are also commercially available (e.g., from Promega Biotech, Inc.).

In vitro transcription of a DNA results in the formation of an RNA transcript, which then may be subjected to in vitro translation to produce NRF or components thereof. In vitro translation of the transcript can be performed in commercially-available free translation systems, such as the rabbit reticulocyte lysate system or the wheat germ system, both commercially available (Promega Biotech, Madison, Wis.) according to the supplier's instructions.

The NRF polypeptide(s) may also be synthesized from a gene or cDNA encoding the polypeptide(s) by coupled in vitro transcription/translation in a procaryotic or eucaryotic cellular system. The DNA is placed in an appropriate expression vector, many of which are commercially available. The vector is introduced into the selected host cell, such as *E. coli*, using widely-known methods, and strains that are commonly available, e.g., *E. coli* strain HB101 or DH5α. Appropriate eucaryotic expression systems, such as yeast expression systems, are also commercially available.

After NRF (or components thereof) has been produced by expression of DNA encoding the factor according to one of the aforementioned methods, it may be further purified. This may be accomplished by affinity purification using appropriate antibodies, according to known methods.

II. Characteristics of NRF and NRFSCI

A. Physical Characteristics of NRF

The molecular weight of the most prominent band of the affinity purified fraction of rat embryonic primordial conditioned medium was found to be approximately 55 kDa, as determined by SDS polyacrylamide gel electrophoresis and Western blotting. Western blotting also revealed less abundant polypeptides appearing in that fraction at approximately 110 and 220 kDa. Both the 55 kDa and the higher molecular weight polypeptides are recovered by affinity purification of the embryonic primordial conditioned medium with anti-NRF antibodies, as visualized after silver staining of a polyacrylamide gel. These higher molecular weight forms are especially apparent in polyacrylamide gels run under non-reducing conditions. If the affinity-purified protein was boiled in SDS and mercaptoethanol, then treated with dithiothreitol, the higher molecular weight polypeptides were diminished in abundance, in favor of the 55 kDa polypeptide. These results suggested that the larger forms are multimers of the smaller form but other explanations are not ruled out (i.e., the larger form could be the native NRF, and the smaller forms could be the subunits thereof).

In addition to being secreted from embryonic primordia in culture, NRF has also been found associated with the cytosol and membranes of adult neurons in vivo. The membrane association may be a stable association, or it may be a transient association of the polypeptide with the protein-secretory pathways of cells. Such pathways involve the association of secreted proteins with membranes of the endoplasmic reticulum, Golgi apparatus and sometimes with secretory vesicles, all of which direct the proteins to the outside of the plasma membrane. Clearly though, as discussed below, secreted, soluble NRF exerts a neurotrophic effect, so a membrane association apparently is not required for activity of the factor.

Immunoprecipitation of the cytosolic homogenate of cortical neurons with the 8G6 antibody yields a fraction (sometimes referred to herein as the "cortex cytosolic affinity fraction or NRFcma") in which the predominant antigenic material is a polypeptide (or complex of polypeptides) migrating at approximately 200–220 kDa on an SDS-polyacrylamide gel under non-reducing conditions. Following HPLC purification of this protein, the protein was found to exhibit neuron growth- and survival-promoting activity at concentrations between 0.5 and 5.0 nM. Physical characterization of the 200 kDa protein (or protein complex) is set forth in detail in Example 7. As discussed in Example 7, it is believed that this species represents the active cytosolic form of NRF, and may comprise the smaller (55 kDa) polypeptide that predominates in the condition medium of embryonic primordia. However, other explanations regarding the relationship of the 200 kDa antigenic polypeptide and the 55 kDa antigenic polypeptide can be made. The presence of the 200 kDa NRF in the affinity-purified fractions of the conditioned medium of embryonic primordia (sometimes referred to herein as the "conditioned medium (CM) affinity fraction, NRFcma") was confirmed by HPLC purification and analysis of biological activity of the 200 kDa band. Accordingly, herein, NRF of the invention refers generally to the larger polypeptide or complex thereof migrating at approximately 200 kDa. It will be appreciated by those skilled in the art that the NRF of the present invention may comprise two or more polypeptides, which may be either identical or non-identical, assembled into a large complex of approximately 200 kDa, and that the complex, as well as one or more of its components, may possess NRF biological activity. Indeed, as discussed below and in Examples 10 and 11, NRFSCI, which is a biologically active component of NRF, has been isolated and characterized in accordance with this invention. Therefore, although NRF may sometimes be referred to as a single protein herein, reference to the factor includes the plural as well as the singular.

As described in detail in Example 7, a partial amino acid sequence of two peptide fragments of a digest of NRF have been obtained. Surprisingly, the amino acid sequence of these peptides was found to be substantially identical to highly conserved sequences of several actins. Moreover, one of the two peptides was also found to be identical in sequence to a tyrosine kinase hybrid that also contains actin sequences (see Naharro et al., Science, 223: 63–66, 1984). Actin sequences have never been associated with neurotrophic factors identified and characterized to date, and therefore serve to further characterize the uniqueness of the NRF of the present invention.

It will be appreciated by those skilled in the art that NRF from species other than rat may vary somewhat in the size of the protein or protein complex (although human NRF appears to be a complex of about 200 kDa). However, it is well known that neurotrophic factors are highly conserved among species, and are generally cross-reactive with antibodies raised against factors from different species. Therefore, polypeptides from other species are expected to be immunologically cross-reactive with antibodies raised against NRF from rat.

B. Physical Characteristics of NRFSCI

As described in Example 10, acid elution of an actin affinity preparation from neural cells yields a unique protein or protein complex, referred to as NRFSCI. Amino-terminal sequence analysis of this protein from human Y9 retinoblastoma cells revealed a novel sequence with little homology to any known sequence.

The behavior of NRFSCI in its purification, along with the amino-terminal sequence information, indicated that the protein is highly acidic and hydrophilic. The protein further demonstrates aggregation characteristics upon varying treatment with detergents, reducing agents and heat. As described in detail in Example 10, it appears that the NRFSCI may be comprised of a fundamental component migrating on a polyacrylamide gel with an approximate molecular weight of about 2.5 kDa (referred to herein as $NRFSCI_{3-4}$ in the presence of SDS and a reducing agent. Without the reducing agent, or upon boiling, the NRFSCI appears to aggregate preferably to an apparent molecular weight of 14–21 kDa (referred to herein as $NRFSCI_{14-21}$) and also to a higher molecular weight of about 66–69 kDa (referred to herein as $NRFSCI_{66-69}$). A single prominent band with an apparent molecular weight of about 7–10 kDa appears in gels run with 0.1% sodium phosphate. This gel system confronts the protein with highly alkaline conditions during electrophoresis, which may destroy sulfhydryls and disulfdes. The intensity of the lower molecular weight bands is increased by treatment with N-ethyl maleimide, also indicating the presence of sulfhydryls. It is believed that this 7–10 kDa peptide is $NRFSCI_{3-6}$.

The NRFSCI has been purified from both human and rat sources, and has been found to possess similar properties. Accordingly, antibodies raised against the NRFSCI from one source will be expected to immunologically cross-react with the NRFSCI from another source.

C. Functional Characteristics of NRF and its Subcomponents

Similar to other known neurotrophic factors, NRF is capable of promoting neurite outgrowth and survival of cultured neurons. This survival and growth-promoting neurotrophic activity can be demonstrated on distinct populations of neurons, and is concentration dependent, based on which neuron population is being subjected to treatment. For example, dissociated embryonic day 17 posterolateral thalamic neurons, which include dorsal lateral geniculate nucleus (dLGN) neurons showed enhanced neurite outgrowth and survival upon exposure to NRFcma in a concentration of the conditioned medium affinity fraction of between 0.1 μg protein per ml to 5.0 μg/ml (see Example 2). At a significantly higher concentration of the conditioned medium affinity-purified material (e.g., 50 μg protein per ml), NRFcma exerts a negative effect on growth and survival of neurons, as compared to untreated control cells. It should be noted that these concentrations refer to total protein concentrations after affinity purification of the embryonic primordia conditioned medium. This affinity purified material may also contain other inert proteins (e.g., albumin, immunoglobulins), so the net effective concentrations of NRFcma may be lower than the values given for the affinity purified material.

In fact, studies conducted with NRF affinity purified from cortex cytosol in accordance with the present invention indicate that NRF can exert a neurotrophic effect on certain neuron populations at a concentration as low as about 100 ng/ml, and usually at concentrations between about 0.1–1.0 μg/ml (0.5–5.0 nm). As described in Example 8, NRF that was HPLC-purified from the cortex cytosol affinity fraction was capable of significantly increasing the survival of cultured anterior thalamic rat neurons at concentrations between 0.1–1.0 μg/ml. It will be appreciated by those skilled in the art, however, that the relative differences in concentration dependence for different neuron populations, as well as concentration curves for particular populations, will remain consistent.

In comparison, the growth and survival of hippocampal neurons at E17 is stimulated by treatment with a broader concentration range of conditioned medium (cm) affinity fraction containing NRFcma, and the optimum concentration for promoting growth and survival of hippocampal neurons is at least 10 fold higher than that found for posterolateral thalamic neurons (i.e., 50 μg/ml of the conditioned medium affinity fraction). Specific populations of neurons possess a NRF concentration-specific dependence on cultured cells, as determined by the in vitro assay described in Example 2.

NRF also rescues neurons from death in adult and newborn mammals after cortical lesions. This rescue is also concentration dependent, as determined by treatments with varying concentrations of the conditioned culture medium containing NRFcm (Eagleson et al., 1990, supra). A concentration of 8 μg protein/ml of the CM affinity fraction, which is in the range of its optimal activity in vitro, when implanted into the cavity of an occipital cortex lesion in newborn rats, was capable of rescuing and regenerating neurons in the lesion, as compared with lesions treated with control medium containing no NRFcm. An example of the results of such an in vivo assay for NRF activity is set forth in greater detail in Example 3.

NRFcm is also capable of rescuing neurons in adults after cortical lesions. In animals treated with control medium applied to the cortical lesion, a 40% loss of neurons in the dLGN can be observed. Upon treatment with 8 μg/ml of the CM affinity fraction containing NRFcm, most of these neurons are rescued. The effect of NRFcm on lesions in the adult cortex is set forth in greater detail in Example 4.

Thus, NRF and subcomponents thereof comprise a neurotrophic factor capable of promoting neuron outgrowth and survival in vitro and of rescuing damaged neurons in the central nervous system in vivo. The neurotrophic effect of NRF extends to a broad range of neuron populations, as demonstrated by its widespread distribution in the normal brain, shown by immunostaining (see Example 5). Therefore, general applicability of NRF to divergent neuron populations is contemplated in this invention. The concentration of NRF effective to promote survival and neurite outgrowth depends on the neuron population being treated. The optimum concentration may be determined by in vitro or in vivo assays, as described in the examples.

In addition to its functionality as a neurotrophic factor, several lines of evidence now indicate that NRF is also a regulatory molecule associated with neurotransmitter receptor/ion channel macro-molecular complexes associated with cell membranes. As described in greater detail in Example 7, an actin-associated ion channel regulatory molecule has been proposed in models explaining the mechanisms by which ion channels operate in excitatory cells such as neurons. NRF possesses the following features indicative of its role as an actin-dependent ion channel regulatory protein: (1) NRF is associated with actin amino acid sequences; (2) NRF is distributed both intracellularly and extracellularly in regions of high glutamate binding during development (indicating co-localization with certain glutamate receptors and/or its requirement as a protective molecule in regions where high levels of potentially toxic neurotransmitters are present; (3) NRF activity is concentration-dependent, consistent with regulatory functions; (4) NRF has hydrophobic regions for interaction with cellular membranes; and (5) NRF survival-promoting activity is completely neutralized by high concentrations of glycine, another amino acid neurotransmitter involved in regulation of ion channels in cellular membranes.

The purification of a separate cytoprotective component of NRFSCI supports the notion that NRF in general, and NRFSCI in particular, may be integrally involved in the relationship between cytoskeletal polymerization, excitotoxicity and neuronal survival, which has become the subject of recent investigation (see, e.g., Furukawa et al., Exp. Neurol. 133: 153–163, 1995). NRFSCI has been tested for its protective effect on a mouse neuronal cell line and on the cerebral cortex of lesioned rats. As described in Example 11, NRFSCI exhibits cytoprotective effects in the femtomolar concentration range in vitro, and in the micromolar range in vivo.

C. Comparison with Other Neurotrophic Factors

The foregoing experimental results indicate that NRF is most likely a soluble complex of factors that is cytosolic or can be released by several distinct neuron populations in the central nervous system. The factor enhances the survival and function of neurons of the central nervous system.

Several neurotrophic factors that have been characterized are listed below in Table 1. NRF and NRFSCI differ distinctly from all the neurotrophic factors listed in Table 1, notwithstanding the fact that all neurotrophic factors share certain characteristics.

TABLE 1

Purified and Partially-Purified Neurotrophic Factors, Their Effects in the Central Nervous System, and Selected Physical Properties

| FACTOR | EFFECTS | PROPERTIES |
| --- | --- | --- |
| Nerve growth factor (NGF)* | survival of cholinergic neurons, neurite induction | MW 13,000 pI 10.0 |
| Ciliary neurotrophic factor (CNTF)* | survival, neurite outgrowth | MW 20,400 pI 5.0 |
| Brain-derived neurotrophic factor (BNDF)* | survival, (additive with NGF) | MW 12,300 pI 10.1 |
| Insulin-like growth factor-II (IGF-II) | survival, neurite outgrowth | MW 7,100 |
| Basic fibroblast growth factor (bFGF)* | survival, neurite outgrowth | MW 16,400 pI 9.6 |
| Acidic fibroblast growth factor (aFGF) | neurite outgrowth | MW 15,800 pI 5.0 |
| Striatal-derived neuronotrophic factor | survival of dopamine cells, neurite outgrowth | MW 14,000 |
| Striatal extract factors | survival of dopamine cells, neurite outgrowth dopamine uptake | MW 1500–2200 |
| Dopaminergic neurotrophic factor | survival of dopamine cells, neurite outgrowth dopamine uptake | MW 9,500 |

The asterisk indicates a factor derived from cells of the peripheral nervous system.

The factors listed in Table 1 may be characterized either as true neurotrophic factors, having the ability to increase the survival of central nervous system neurons, or as neurite-promoting factors, capable of enhancing neurite outgrowth, but having no particular effect on survival of neurons. Among the factors listed in Table 1, the following are capable of promoting both neurite outgrowth and neuron survival: (1) nerve growth factor (NGF); (2) ciliary neurotrophic factor (CNTF); (3) brain-derived neurotrophic factor (BNDF); (4) insulin-like growth factor-II (IGFII); (5) striatal-derived neurotrophic factor; (6) striatal extract factors; and (7) dopaminergic neurotrophic factor (DNTF). NRF is physically distinguishable from each of the aforementioned neurotrophic factors. The NRF complex has a molecular weight of ~200 kDa which, insofar as is known, is the largest neurotrophic factor or complex to have been characterized. Of the neurotrophic factors listed in Table 1, ciliary neurotrophic factor (CNTF) is the largest, and its molecular weight is only 20,400 Da.

An additional distinguishable characteristic of NRF is that the 8G6 antibody, which is immunologically specific for the factor, does not cross-react appreciably with other neurotrophic factors. Neurotrophic factors that have specifically been tested for cross-reactivity to the 8G6 antibody include NGF, CNTF, basic FGF and acidic FGF, none of which were found cross-reactive with the antibody. This observation is significant of the uniqueness of NRF in view of the fact that many of the neurotrophic factors listed in Table 1 are antigenically similar (i.e., antibodies raised against one of the factors tends to cross-react with the other factors). The lack of cross-reactivity of anti-NRF antibody with other neurotrophic factors is therefore highly indicative of the physical uniqueness of this molecule.

Another distinguishing characteristic of NRF was discovered by obtaining partial amino acid sequences of certain regions of the polypeptide or polypeptide complex. As discussed above, the sequences show a high level of homology with highly conserved sequences of various actins. Additionally, one of the polypeptides shows sequence homology with an actin-containing tyrosine kinase. No other neurotrophic factor has been characterized as having actin-containing sequences. Hence, the presence of these sequences in NRF further contributes to the unique physical characteristics of the factor.

$NRFSCI_{14-21}$, although of a size range similar to other neurotrophic factors, also possesses several unique characteristics not shared by other known neurotrophic factors. Its tight association with cytoskeletal components, such as actin epitopes, is one such feature. More importantly, however, the amino terminal sequence of $NRFSCI_{14-21}$ is unlike any other presently known neurotrophic factor.

Thus, although there are numerous neurotrophic factors that have biological activity in the central nervous system, the apparent differences in physical properties, as well as the various differences in functional features between those factors and NRF or subcomponents thereof strongly indicates that NRF is a novel neurotrophic growth factor and $NRFSCI_{14-21}$ is a unique cytoprotective protein.

II. Uses of NRF Antibodies Raised Against NRF or subcomponets thereof and Nucleic Acid Molecules Encoding NRF or its Subcomponents NRF or its subcomponents, as well as antibodies raised against the factor and nucleic acid molecules encoding the factor, have broad utility in the diagnosis and treatment of neuron damage and neurodegenerative disease. The uses of these materials described hereinbelow are intended to exemplify their utility, and are not intended to limit the invention.

It has been discovered in accordance with the present invention that NRF and its subcomponents promote survival and neurite outgrowth of neurons in culture and rescues damaged neurons of the central nervous system in vivo. Thus, as a pharmaceutical preparation, NRF or its subcomponents can be used to advantage in the treatment of neurodegenerative diseases and disorders. Such diseases and disorders include, but are not limited to (1) trauma, (2) stroke, (3) nonspecific anoxia (i.e., anoxia due to drowning, suffocation, etc.), (4) neurodegenerative diseases such as Alzheimer's disease, Parkinson's disease and amyotrophic lateral sclerosis (ALS); and (5) mental retardation syndromes associated with progressive neuronal degeneration (e.g., cerebral palsies).

In addition, because NRFSCI appears to contain highly reactive sulfhydryls, which are known to target dangerous oxygen free radicals, NRFSCI is expected to exert a protective effect on a wide variety of non-neural cells whose function may be compromised by ischemia, anoxia or toxemia. Thus, $NRFSCI_{14-21}$ may used to protect against cellular degeneration arising from heart or artery disease, kidney failure or liver degeneration, to name a few examples. $NRFSCI_{3-6}$ is also expected to exert a protective effect.

A pharmaceutical preparation of NRF and/or its subcomponents is formulated for administration to patients by combining the factor with a biologically acceptable medium, such as water, buffered saline, or osmotically-adjusted media such as polyol (e.g., glycerol, propylene glycol, liquid polyethylene glycol and the like) or suitable mixtures thereof. The term "biologically acceptable medium" includes all solvents, dispersion media and similar components which may be appropriate for the selected route of administration of the pharmaceutical preparation. The use of such biologically acceptable media for pharmaceutical preparations is well known in the art. Unless a conventional medium or agent is incompatible with the active ingredient of NRF or any of its subcomponents, its use in the pharmaceutical preparation of the invention is contemplated.

In a preferred embodiment, solutions comprising NRF or subcomponents thereof are incorporated into a solid matrix, which can be implanted into regions of the brain requiring treatment. As described in Example 3, a pre-determined concentration of NRF may be mixed in equal parts with a 2% sodium alginate medium, and is entrapped in the resulting gel matrix. The sodium alginate gel is polymerized in the form of small beads by dropping the gel into a 0.5 M $CaCl_2$ solution. Other solid or semi-solid biologically compatible matrices are also contemplated for use in the present invention. These include various natural bio-polymers, such as xanthan and carob gums (See Mugnier et al., Appl. Environ. Microbiol., 50: 108–14 (1985).

The pharmaceutical preparation comprising NRF or subcomponents thereof is advantageously formulated in dosage units, which is defined herein as a discrete unit of the pharmaceutical preparation appropriate for the patient undergoing treatment. As used herein, the term "patient" refers to humans and animals. A dosage will contain the quantity of active ingredient determined to produce the desired therapeutic effect in conjunction with the selected pharmaceutical carrier.

The appropriate dosage of a pharmaceutical preparation comprising NRF or subcomponents thereof as the active ingredient is determined by in vitro and in vivo procedures, as described in the Examples. As discussed earlier, the optimum effective concentration of NRF is dependent upon the type of neuron being treated and the protocol and source used for purification. Therefore, once the target neuron population has been identified, the optimum effective concentration of NRF should be determined by one of the in vitro assays described in the Examples. In the assays, the selected neuron population is grown in culture for 2–4 days in defined serum-free medium. Pre-determined concentrations of NRF in an appropriate biological medium is added to the culture dishes every 24 hours. After the incubation period, neurons and dendrites are identified. This can be accomplished immunocytochemically, e.g., with an antibody against a neuron-specific marker, such as MAP2. Neuron survival and neurite outgrowth is then determined. By comparing the effect of each concentration of NRF on neurite outgrowth and neuron survival, an optimum concentration for the specific neuron population is determined. In one embodiment, it was determined that 0.5–5 μg/ml of the affinity-purified NRFcm fraction from embryonic primordia enhanced the survival and neurite outgrowth of E17 posterolateral thalamic neurons of rats, as described in Example 2. In an alternative embodiment, it was determined that approximately 50 μg protein/ml of the CM affinity fraction containing NRF enhanced neurite outgrowth and neuron survival of hippocampal neurons (also described in Example 2). In a preferred embodiment, HPLC-purified NRF from the cytosol of cerebral cortex cells or from cultured human retinoblastoma cells, NRFrb, was found to be effective on anterior and/or posterolateral thalamic neuron populations at a concentration ranging from 0.5–5.0 nM.

After the optimum in vitro concentration of NRF has been determined for a specific neuron population, an appropriate dosage may be deduced by in vivo assay on laboratory animals, such as rats (see Examples 3 and 4). For example, it was determined that two alginate beads containing 8 μg (total protein)/ml of the embryonic primordial CM affinity fraction containing NRFcm was an appropriate effective concentration for rescuing damaged dLGN neurons in the posterior cortex of newborn rats. In an independent assay of adult rats having lesions of the visual cortex, infusion of the 8 μg/ml CM affinity fraction into the lesioned cavity by Alzet minipump was found effective to rescue the damaged dLGN neurons that project to the visual cortex. An appropriate dosage based on the brain area damaged can be calculated from the absolute concentrations required for effective rescue of degenerated neurons in tests on laboratory animals. For example, as described in Example 3, a lesion that damages 2 $cm^3$ of part of the visual cortex involved in central vision of a rat required approximately 200 μl of CM affinity fraction containing NRFcm, at 8 μg total protein/ml, for rescue of the dLGN neurons that would usually die as a result of such a lesion. An equivalent lesion in a primate or human would damage approximately 15-fold more cortical tissue. The area of brain damage is determined by standard imaging techniques, e.g., MRI. Therefore, that lesion cavity must be treated with an approximately 15-fold greater amount of the factor.

Based on in vitro and in vivo studies on mice, $NRFSCI_{14-21}$ is estimated to have from about 20 to 400 times the specific activity of NRF (0.02–0.5 μg/ml versus 8 μg/ml). Thus, dosages of the $NRFSCI_{14-21}$ for primates or humans would be adjusted accordingly using standard methods as describe above.

The pharmaceutical preparation is preferably administered parenterally, by introduction into the central nervous system of the patient. This may be accomplished by intracerebroventricular infusion targeted to the location of neuron damage. Alternatively, a solid matrix containing the appropriate dosage of NRF may be implanted into a damaged region of the central nervous system. Other methods may also be utilized to administer a pharmaceutical preparation containing NRF or subcomponents thereof. Administration may be by any method that allows NRF or its subcomponents to cross the blood/brain barrier, either alone or linked to a carrier, including injection into the bloodstream, as well as oral, intranasal, rectal and ophthalmic administration.

A pharmaceutical preparation containing NRF or its subcomponents may be administered as a one-time dosage for cases of acute anoxia or trauma, or it may be administered at appropriate intervals in the case of chronic degenerative disease, until the symptoms of the disease are reduced or eliminated. The appropriate interval of administration of the pharmaceutical preparation will depend on the type of neuron damage being treated and the condition of the patient.

NRF or its subcomponents may also be useful for diagnostic applications. Neurons that are natural targets for NRF in vivo will likely possess receptors for the factor on their surfaces. Certain neurodegenerative disorders may result from a lack of such receptors on cell surfaces. NRF may be labelled by any standard means and used for binding assays to determine the ability of certain neuron populations to bind the receptor. Thus, abnormally low binding of the factor to a certain neuron population or neurons from a diseased subject may be determined.

Antibodies that react immunospecifically with NRF or its subcomponents are particularly useful for purification and diagnostic procedures. These utilities include affinity purification of NRF or its subcomponents from conditioned medium or other sources, such as cytosol or membranes, as well as the use of antibodies to screen nucleic acid expression libraries for genes or cDNAs encoding the factor, or components thereof. Antibodies may also be used for diagnostic applications. For example, anti-NRF or anti-NRFSCI may be used for immunostaining of normal brains to determine the localization and distribution of NRF in different areas of the brain. Neuron populations identified by immunostaining would be likely targets for treatment by administration of pharmaceutical preparations containing NRF or its subcomponents.

As discussed above, nucleic acid molecules, including genes, cDNA or RNA, that encode NRF or a component thereof can also be used for a variety of purposes. In a preferred embodiment, a cDNA or gene is used for producing large quantities of NRF by recombinant DNA techniques. Preparation by gene expression is advantageous because of the large quantities of protein that can be produced in this manner, as well as the production of the proteins in a form that is substantially purified from any other neurotrophic factor or neuronal protein.

Oligonucleotides that are complementary to part or all of a nucleic acid encoding NRF are useful for diagnostic applications. Such molecules, often referred to as "antisense" oligonucleotides, can be used in in situ hybridizations to determine where NRF is encoded and expressed in normal or diseased brains. Such antisense oligonucleotides may also be useful for blocking expression of NRF or one of its components, either for diagnostic application, or for treatment of pathologic conditions involving overexpression of the factor.

In summary, NRF (and particularly its $NRFSCI_{14-21}$ component) possesses a broad-based applicability as a pharmaceutical agent for treatment of damaged or degenerating neurons. As discovered in accordance with the present invention, it can be used to treat widely divergent neuron populations, once an effective concentration has been determined. NRF and $NRFSCI_{14-21}$ are easily identifiable on the basis of unique characteristics. Additionally, both in vitro and in vivo assays are available for testing the effectiveness of NRF and $NRFSCI_{14-21}$ on specific neuron populations. Antibodies immunospecifically reactive with NRF or its subcomponents, as well as nucleic acid molecules and fragments thereof encoding part or all of NRF, also possess a variety of utilities, including the purification and/or production of NRF or its subcomponents in large quantities, as well as diagnostic and therapeutic applications.

The following examples are provided to describe the invention in further detail. These examples are intended to illustrate and not to limit the invention.

EXAMPLE 1

Preparation of NRF from Conditioned Culture Medium of Embryonic Primordia Comprising the Geniculocortical Pathway A. Preparation of Conditioned Medium Timed pregnant Long-Evans rats were anesthetized with chloral hydrate (35 mg/100 g body weight) late on Embryonic Day 14 (E14 with the first day postconception considered E1). Under aseptic conditions, the posterior 1⅓ of the telencephalon and the caudal half of the diencephalon were dissected from each embryo and the meninges were carefully removed.

Each cortical explant was cocultured with a diencephalic explant. The explants were placed 3–5 mm apart in a 35-mm Falcon Primaria culture dish containing 1.1 ml of culture medium. The culture medium was composed of 90% Ham's F10 (25 mM Hepes buffered) and 10% Nu Serum (Collaborative Research) to which were added the following supplements (with final concentrations indicated): 0.1% MITO+ (Collaborative Research, Bedford, Mass.), β-glycerophosphate (200 μg/ml), taurine (2 μg/ml), carnitine (1 μg/ml), PABA (1 μg/ml), citrate (20 μg/ml), succinate (10 μg/ml), galactose (200 μg/ml), fructose (100 μg/ml), BSA-linoleic complex (6 μg/ml), thiamine monophosphate (1 μg/ml), triethanolamine (2 mM), L-glutamine (2 mM), and sodium bicarbonate (3.7 μg/ml). After explanting, the cultured dishes were maintained at 33.5–34.5° C. in a 90% air/10% $CO_2$ high humidity atmosphere. Unconditioned control medium was prepared by placing an identical amount of culture medium into culture dishes without tissue.

After five days in vitro, approximately 0.7 ml of medium was collected from each dish and pooled. Media collected in several different culturing sessions, with each batch of medium treated separately and identically, was pooled. The culture medium was filtered through a 0.22μm Millex-GV filter (Millipore, Bedford, Mass.) and then concentrated by a factor of 25 by pressure ultrafiltration through a membrane with a 10-kDa molecular weight cut-off (Pharmacia, Piscataway, N.J.). The macromolecular fraction (i.e., the fraction containing molecules greater than 10 kDa) was used immediately for further purification or stored as frozen droplets in liquid nitrogen.

B. Affinity Purification of NRF from Conditioned Medium

The macromolecular fraction of the conditioned medium was subjected to high performance liquid chromatography (HPLC), using a Superose 12 column (Pharmacia), which allows for size exclusion in an aqueous environment. 1 ml fractions were collected, and measured for absorbance at 280 nm to identify fractions containing protein. Each of these fractions was tested for neurotrophic activity by the in vivo assay described in Example 3. Once the active HPLC fraction was identified, approximately 100 ml of this fraction from numerous HPLC runs was collected and concentrated for the purpose of producing monoclonal antibodies.

The concentrated fraction was used for footpad immunization of mice and subsequent nodal fusion, according to standard procedures for monoclonal antibody production. Resultant clones of hybridoma cells were screened initially with the conditioned medium as well as with a similar fraction of unconditioned medium and with serum albumin (another protein synthesized by the cultured cells and released into the conditioned medium).

Two clones (8G6, 7F3) out of 487 were identified that recognized only the conditioned medium HPLC fraction. Isotyping revealed that both were $IgG_1$ subclass. Both 8G6 and 7F3 produced identical immunological results; therefore, subsequent manipulations were performed only with the 8G6 monoclonal antibody.

The conditioned medium was subjected to polyacrylamide gel electrophoresis and Western blotting with the 8G6 monoclonal antibody, according to standard methods. Western blotting of the conditioned medium revealed a prominent band at approximately 55 kDa and lighter-staining bands at approximately 110 kDa and 200–220 kDa. The antibody was found not to cross-react with nerve growth factor (NGF), ciliary neurotrophic factor (CNTF), basic fibroblast growth factor (bFGF) or acidic fibroblast growth factor (aFGF). Moreover, the apparent molecular weights of the proteins in the conditioned medium precluded the active factor from being identical with such factors as BNDF, NT-3 or any interleukins with known neurotrophic effects.

The 8G6 monoclonal antibody was linked to a protein A-sepharose column for immunoaffinity purification of NRF from the conditioned medium, according to the method of Zacco et al., J. Neurosci., 10: 73–90 (1990). This affinity-purified material is referred to herein as the "CM (conditioned medium) affinity fraction or NRFcm." The proteins collected in the CM affinity fraction were separated by polyacrylamide gel electrophoresis.

C. Physical Characterization of Proteins Collected by Affinity Purification of Embryonic Primordia Conditioned Medium Silver staining of the polyacrylamide gel of the CM affinity fraction revealed two prominent protein bands at approximately 55 and 110 kDa, and a third band at approximately 200–220 kDa. To determine if the bands isolated by immunoaffinity purification were actually one or more forms of the neuron regulatory factor synthesized by cells in the conditioned medium-producing explants, the following procedure was performed. The cortex/diencephalon-cultures were incubated with $^{35}S$ methionine (200 μci/ml) for the last 6 hours of the 5 day culturing period. Following affinity purification and exposure of gels to x-ray film, both the 110 kDa and 55 kDa polypeptide bands appeared on the autoradiographs. It was found that boiling the affinity-purified protein in SDS and mercaptoethanol, followed by treatment with dithiothreitol diminished the higher molecular weight bands in favor of the 55 kDa band, indicating that the larger forms may be multimers of the smaller form. However, other possibilities exist, such as: (1) the smaller forms are subunits of the larger form, which is degraded upon boiling; and (2) the smaller forms are not related to the larger form.

The 200 kDa polypeptide was further purified and tested for neuron trophic activity, as described in Example 7 below, hereinafter referred to as $NRF_{cm200}$. From these experiments, we concluded that the 200 kDa polypeptide was the major active protein in the CM affinity fraction, having the highest specific activity when further purified from the 55 or 110 kDa proteins. The neurotrophic activity of purified 55 kDa and 110 kDa polypeptides has not been determined.

EXAMPLE 2

In Vitro Assay to Determine Concentrations of Conditioned Medium Affinity Fraction Effective to Promote Neurite outgrowth and Survival of Selected Neuron Populations A. Posterolateral Thalamic Neurons Posterolateral thalamic neurons, which include dorsal lateral geniculate nucleus (dLGN) neurons, were harvested from E17 rats, seeded at low density ($4 \times 10^4$ viable cells/ $cm^2$), and grown on polylysine coated coverslips for 48 or 96 hours. The cells were incubated in defined serum-free medium (N2), as described by Bottenstein, Growth and Differentiation of Neural Cells in Defined Media, *Cell Culture in the Neurosciences*, J. E. Bottenstein and G. Sato, eds., Plenum Press, New York, pp. 3–43 (1985). Fractions from the 8G6 affinity column, described in Example 1, showing NRF immunoreactivity on dot blots were pooled and concentrated to produce the CM affinity fraction. Although a small amount of albumin is present in the fraction, the 55, 110 and 220 kd bands associated with NRF activity together comprise more than 80% of the total protein, on the basis of silver stained gels. The CM affinity fraction was added to the dishes in various concentrations every 24 hours. Controls consisted of N2 medium alone or N2 medium with an equivalent added concentration of the elution buffer used in affinity purification.

Following incubation with the CM affinity fraction, neurons and dendrites were identified immunocytochemically. The cells were fixed, treated with 0.1% triton X-100, and stained with an antibody against MAP2, a neuron-specific marker. MAP2-containing neurons and their processes were counted in 15 systematically-defined microscope fields at X630 magnification.

The effect of adding different concentrations of the CM affinity fraction to cultures of E17 posterolateral thalamic neurons is shown in FIG. 1. The y-axis of the graph represents the number of MAP2-positive cells at four different concentrations of NRFcm, expressed as a percentage of the control, in which neurons were incubated in the N2 medium alone. The data are from three different culturing sessions with duplicates for each concentration in each session. As can be seen from FIG. 1, neuron survival was concentration-dependent, survival being enhanced by between 0.5 and 5 μg protein/ml of the CM affinity fraction ($p<0.05$ by the Mann-Whitney U Test). In comparison, incubation of the neurons with 50 μg protein/ml CM affinity fraction resulted in significantly fewer cells surviving ($p<0.1$ by the Mann-Whitney U Test).

Neurite outgrowth was also enhanced at 0.5–5 μg protein/ml of the CM affinity fraction and inhibited at 50 μg/ml. The same effect was observed at 4 days in culture.

It was also observed that the neurite outgrowth and neuron survival-promoting activity of NRF could be neutralized by adding Fab fragments prepared from the 8G6 antibody described in Example 1. Such Fab fragments interact immunospecifically with the NRF antigen, thereby preventing NRF from exerting its effects on the cultured cells. Neutralization of NRF activity indicates that the neuron survival and neurite outgrowth-promoting effects are in fact mediated by NRF in the CM affinity fraction.

B. Hippocampal Neurons

Hippocampal neurons were harvested from E17 rats and grown under identical conditions as described for the thalamic neurons in Part A above. These neurons were incubated with a similar concentration series of CM affinity fraction containing NRFcm.

Figure 2:
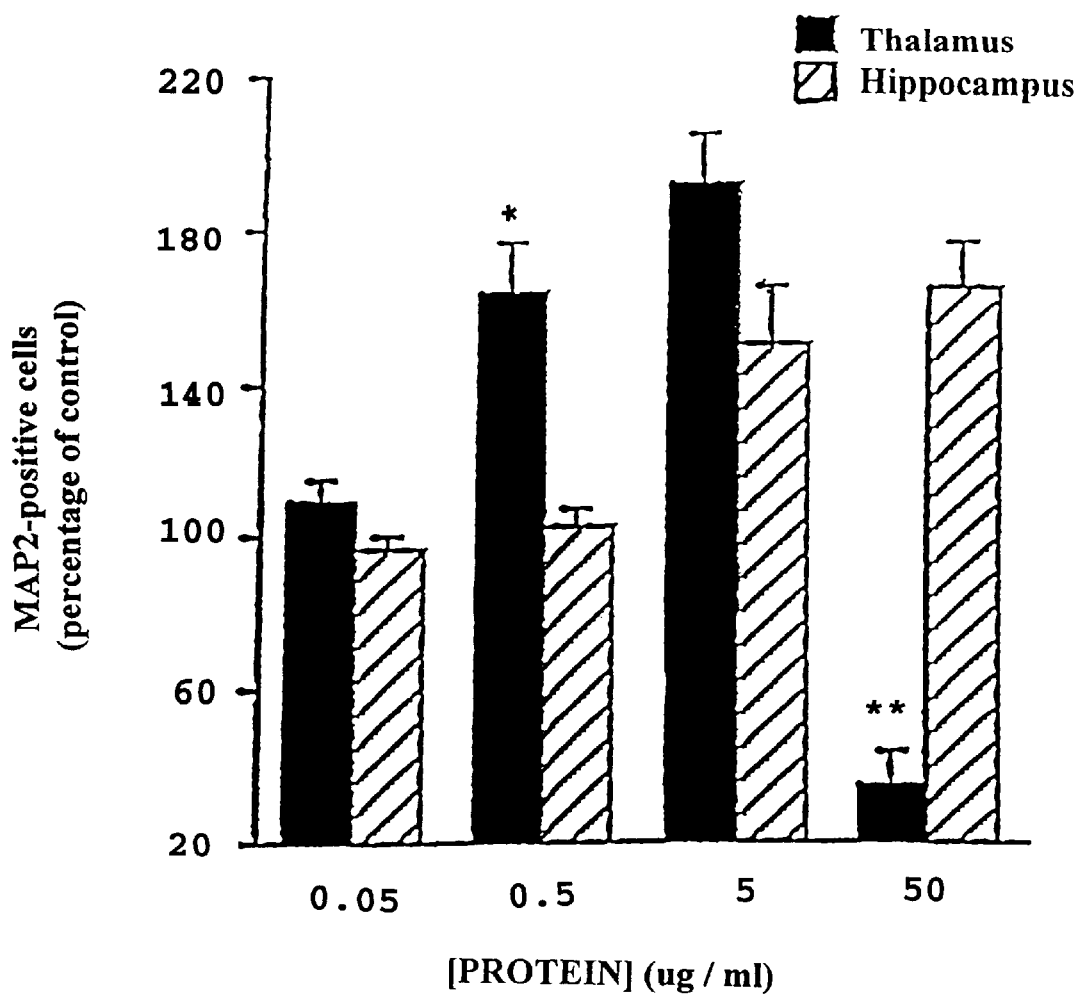
FIG. 2 is a graph comparing the different responses of hippocampal and posterothalamic neurons to increasing concentration of affinity purified NRFcm from embryonic primordia CM, x-axis represents protein concentration of CM affinity fraction containing NRFcm ($\mu$g/ml); y-axis represents the number of neurons, expressed as a percentage of control treatment; solid black bar=thalamus neurons, diagonal lined bar=hippocampus neurons.

It was found that the CM affinity fraction was capable also of promoting the survival and neurite outgrowth of hippocampal neurons. However, as shown in FIG. 2, the range of concentrations that supported hippocampal neurons was broader and at least 10 fold higher than the effective range for posterolateral thalamic neurons. FIG. 2 displays the different responses of hippocampal and posterolateral thalamic neurons to increasing concentrations of CM affinity fraction, NRFcm. The survival of MAP2-positive cells in 48-hour cultures of either E17 hippocampal (diagonal-lined bars) or E17 posterior thalamic neurons (black bars) is displayed. Survival is expressed as a percentage of that found in N2 medium alone and is from duplicate cultures in 3 (hippocampus) or 4 (thalamus) culturing sessions. Statistical comparisons at 5 and 50 $\mu$g/ml are by the Mann-Whitney $\underline{U}$ Test adjusted for multiple comparison by Ryan's procedure.

EXAMPLE 3

In Vivo Assays to Determine Concentrations of Conditioned Medium Affinity Fraction Containing NRFcm Effective to Promote Survival of Damaged Neurons in the Central Nervous System A. Preparation of a Pharmaceutical Preparation Comprising NRFcm as the Active Ingredient in the CM Affinity Fraction Different concentrations of the CM affinity fraction were mixed in equal parts with 2% sodium alginate and thus became entrapped in the resulting gel matrix. The gels were polymerized in the form of small beads in a 0.5 M $CaCl_2$ solution. The beads were quickly rinsed in distilled water and then stored at 4° C. for use within 3 hours.

B. Surgical Procedures

Timed-pregnant female Long-Evans rats were labelled with [$^3$H]-thymidine (10 $\mu$Ci/g body weight) on either the 14th or the 15th and 16th days of gestation, which spans the period of dLGN neurogenesis in the hooded rat. Within 18 hours of birth, the labelled neonates were anesthetized by hypothermia and placed on a cold pack. The right posterior cortex was then exposed. The entire right occipital cortex was removed by a suction lesion that extended to the underlying white matter. Gelfoam (Upjohn, Kalamazoo, Mich.), soaked in the same concentration of CM affinity fraction containing NRFcma as that loaded into the alginate beads, was packed along the lateral margin of the lesion. Two alginate beads were then placed in the lesion cavity on the remaining white matter overlying the dorsal surface of the hippocampus. The remainder of the lesion was covered with another piece of CM affinity fraction-soaked gel foam and topped by the host's skull flap and the overlying skin was sutured. The animals were then warmed under a lamp and returned to the dam.

C. Analysis of dLGN Survival

On post-natal day 6, the rats were anesthetized by hypothermia and then perfused with phosphate-buffered formalin. Brains were frozen for cryostat sectioning and alternate 20$\mu$m coronal sections were collected through the entire posterior thalamus. The sections were mounted on glass slides and dipped in Kodak NTB-2 nuclear emulsion. All slides were exposed for two weeks, then developed and stained with cresyl violet.

The dLGN was defined cytoarchitectonically, using the surrounding fiber tracts and nuclei as additional markers. The surviving neuron-occupied volume of the dLGN and the number of [$^3$H]-thymidine-labelled cells remaining were compared in rats treated with different concentrations of CM affinity fraction containing NRFcm. The total volume of the dLGN both ipsilateral and contralateral to the lesion was calculated from planimetric measurements of camera lucida drawings of the coronal sections at 160$\mu$m intervals. The dLGN volume on the operated side is expressed as a percentage of the dLGN volume on the unoperated side. This simple volume measurement provides a rapid and reliable assay of the overall extent of dLGN neuron survival and, if anything, underestimates the actual percentage of identified dLGN neurons that survive the lesion.

The numbers of [$^3$H]-thymidine-labelled neurons in the dLGN were calculated from counts of heavily labelled cells (>15 grains/nucleus). The raw counts were corrected using Abercrombie's procedure (M. Abercrombie, Anat. Rec., 94: 239–47, 1946), with section thickness estimates to be 2 $\mu$m, which is the upper limit of the distance a $\beta$ particle can travel in a tissue section. As with the volume, neuron numbers were expressed as a ratio of operated to unoperated side. For both the volume and cell number measurements, all mean values are expressed as ±SEM, and all statistical comparisons utilized the Mann Whitney $\underline{U}$ test, adjusted for multiple comparisons by Ryan's procedure (R. E. Kirk, Experimental Design: Procedures for the Behavorial Sciences, pp. 494–97; Brooks/Cole, Belmont, Calif., 1968).

The aforementioned analysis at day 6 after treatment revealed that, when the dLGN in untreated animals has virtually disappeared, animals with implants of NRFcm from the conditioned medium show a significant increase in dLGN neuron survival. This survival-promoting activity was optimal at a concentration of 8 $\mu$g total protein/ml in the CM affinity fraction, which is in the range of its optimal activity for the CM affinity fraction in vitro. In this same assay system, NGF and bFGF were not active.

EXAMPLE 4

In Vivo Assay to Determine the Effective Concentration of Conditioned Medium Affinity Fraction Containing NRFcm on Damaged Neurons in Adult Rats A pharmaceutical preparation comprising NRFcm in the CM affinity fraction was prepared. A small population of adult Long-Evans rats were typically utilized to provide data for each assay. One group comprised a normal control group; a second group received lesions of the rostral and occipital cortex in the right hemisphere followed by implantation with osmotic pumps containing NRF at predetermined concentrations; and the third group received similar lesions and pump implants containing the unconditioned control medium (vehicle). The operated animals had been labelled in utero with [$^3$H]-thymidine. For thymidine labelling, two pregnant dams at 15 days gestation (E15, with the first day post-conception considered E1) were anesthetized with chloral hydrate (35 mg/ml) and injected intraparenterally with [$^3$H-thymidine (1 mCi/100 g body weight, specific activity equaled 65–80 Ci/mmole). Such injection at E15 results in heavy neuronal labelling of a specific population of dLGN neurons.

When mature, the thymidine-labelled animals were anesthetized using chloral hydrate as above, and placed in a stereotaxic apparatus. The skin overlying the skull was reflected and a medial-lateral strip drilled across the skull over the right posterior cortex at 4.2 mm posterior to Bregma. Using a metal cannula with a 1 mm diameter opening, a suction lesion was then made in the cortex, extending from 1.2 mm to 4.8 mm lateral of the midline. The suction cannula was attached to a metered vacuum line, and a constant pressure was used in making the lesions in all animals.

The lesion cavity was packed with Gelfoam soaked in unconditioned medium, and an osmotic mini pump (Alzet #2002) was implanted, using the procedure of Eagleson et al., Experimental Neurology, 116: 156–62 (1992). The average expected delivery time for the contents of the pump (200 μl at 8 μg protein/ml CM affinity fraction containing NRFcm) was 19.5 days, based on the nominal pumping rates and reservoir volumes for the mini pumps used.

The overlying skin was then sutured, and the animals placed on a heating pad for 1–2 hours, then returned to their cages after receiving an injection of ampicillin (2 cc intramuscularly).

Figure 3:
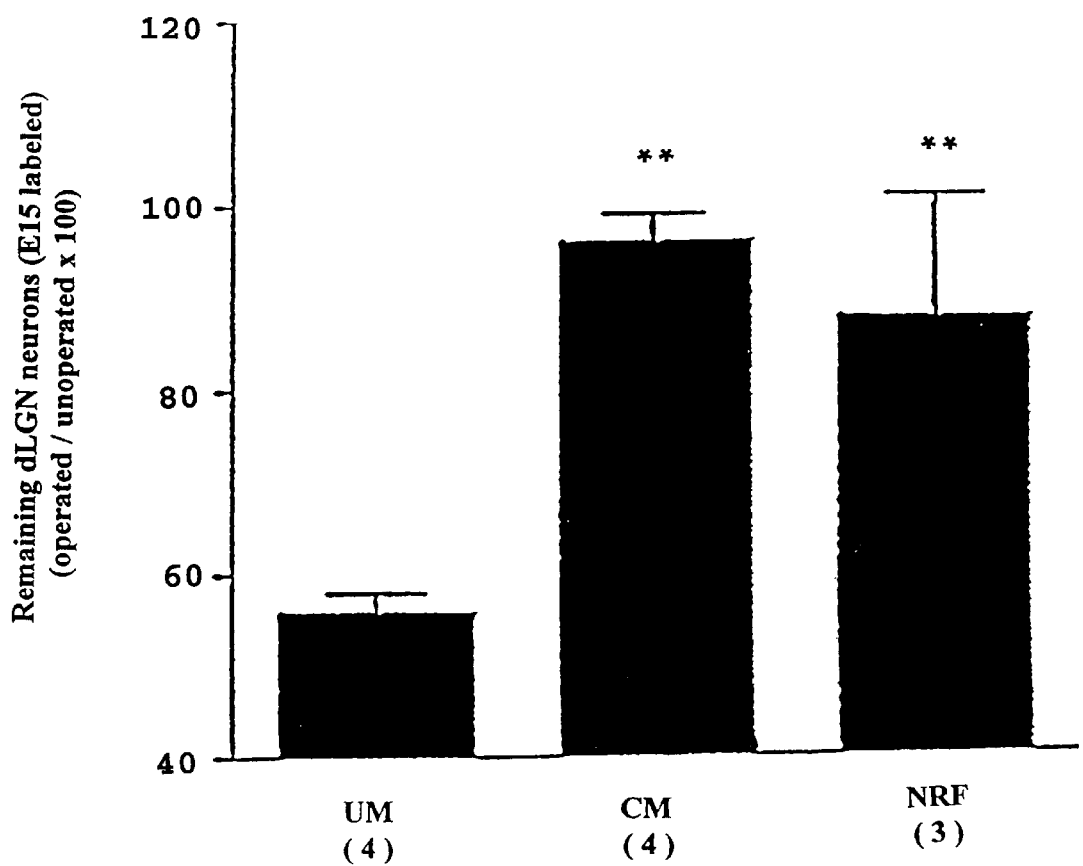
FIG. 3 is a histogram comparing the rescue of dLGN neurons after occipital cortex lesions in adult rats, when treated with: (1) unconditioned medium (UM) (4 animals), (2) conditioned medium (CM) containing unpurified NRFcm (4 animals), and (3) affinity-purified CM containing NRFcm (3 animals); T-bars=range among experimental animals; *=statistically significant values.

As shown in FIG. 3, the CM affinity fraction containing NRFcm rescued dLGN neurons after occipital cortex lesions in adult rats. The graph shows the survival of neurons labelled on embryonic day 15 (E15) after a cortical lesion at the area 17/area 18a border. In the assay exemplified by FIG. 3, the animals were 60 days old at the time of the lesion. Osmotic mini pumps were loaded with either the conditioned medium containing NRFcm described in Example 1, a similarly prepared fraction of unconditioned medium or the CM affinity fraction at 8 μg protein/ml in the unconditioned medium (N=number of rats in each group). The cannulae of the pumps were directed into the lesion cavity and the animals killed for autoradiography and cell counting 2 weeks later. Statistical comparisons are to treatment with unconditioned medium, using the Mann-Whitney test. As can be seen from FIG. 3, in animals with control unconditioned culture medium applied to the lesion, there is a 40% loss of neurons in the dLGN. Application of the CM affinity fraction containing NRFcm at 8 μg protein/ml resulted in the rescue of most of these neurons. A similar result was obtained with the conditioned medium from which the factor was affinity purified.

EXAMPLE 5

Immunocytological Localization of NRP in the Normal Rat Brain

Immunocytochemical staining was employed to determine locations in the brain where NRF is naturally produced and accumulated to an immunocytochemically detectable level, and may be most effective in rescuing damaged neurons. Normal rats were perfused with 2% paraformaldehyde in phosphate buffer in post-natal days 1 (5 animals), 3 (2 animals), 5 (4 animals), 10 (4 animals), 15 (2 animals), and 90 (1 animal). Frozen sections through the forebrain and thalamus were cut at 50 μm on a sliding microtome, then incubated with hybridoma supernatant containing the 8G6 monoclonal antibody, and processed according to standard techniques. Normal goat serum was used for blocking non-specific staining, and is preferred over dried milk for increasing the overall consistency of staining from one brain to the next and the intensity of specific staining in individual brains. Control sections incubated only with horseradish peroxidase-conjugated secondary antibody were prepared for each case. Other controls included incubating the 8G6 antibody with the CM affinity fraction containing NRFcm prior to staining. This effectively blocked the binding sites on the antibody, which severely attenuated staining.

At all ages examined through post-natal day 10, the pattern of NRF immunoreactivity in the forebrain and thalamus was found to be similar. The following description of 8G6 antigen distribution applies to all animals up to 10 days of age, at which time the staining is often more dense, but still shows the same distribution pattern. A rostral-caudal series through the animals' brains revealed the relative distribution and amounts of the factor as follows.

1. Staining in the cerebral cortex appeared in patches. The patches were found throughout the rostral-caudal extent of the neocortex and could vary in density and medial-lateral extent. Medial frontal cortex (area 8), anterior cingulate cortex (area 24), area 18a of occipital cortex, and olfactory bulb were the most consistently stained cortical regions, in that there was dense staining that consistently occupied a large part of the areal extent and all layers of these regions.

2. Patches of more variable density and mediolateral extent appeared in somatomotor cortex (areas 2, 4 and 10), areas 17 and 18b of occipital cortex and areas 40 and 41 of temporal cortex.

3. Hippocampus, subiculum, periform cortex, amygdala, retrosplenial cortex and entorhinal cortex also showed some patches of staining, but these tended to be the most variable in density and extent and were sometimes absent.

4. The medial septal nuclei and dorsal striatum were usually stained. More variable staining (sometimes absent) was found in the diagonal band and internal division of globus pallidus.

5. Most thalamic nuclei were unstained. The exceptions were the anterior nuclei, rostral part of the lateral dorsal nucleus, as well as scattered cells among mid-line groups (mid-line staining could extend into the brain stem). The arcuate nucleus in the hypothalamus was also stained.

The cellular distribution of NRF in rat brains indicates that it is present within developing neurons and in the space surrounding these neurons. In the dense neocortical patches of NRF immunoreactivity, staining is found between and within cells in all cortical layers but the most prominent intracellular staining is within pyramidal cells of layers III and V, and the cells in layer VIb. Additionally, immunopositive cells have been found in purified neuronal cultures of PND3 medial frontal cortex neurons, which further indicates that NRF is contained in, and probably synthesized by, young neurons. In this latter example, NRF is also seen associated with the neuronal surface even in cells not treated (e.g. with 0.1% Triton-X) so as to make their membranes permeable to the 8G6 antibody.

By post-natal day 15, all staining had virtually disappeared, although lightly stained pyramidal cells could sometimes be detected in those cortical areas that showed dense immunoreactivity at earlier ages.

The above-described anatomical results (i.e., consistent differences in staining between some areas and more variable patterns in others) are believed to reflect regional regulation of the levels of NRF. In addition, both the consistent patterns and the variability may relate to the development of synaptic activity in these different regions. In fact, the anatomical distribution of the 8G6 antigen overlaps considerably with areas showing high glutamate binding during post-natal development of the rat forebrain and thalamus. For example, anterior thalamus frontal cortex, CA1 and CA3 of hippocampus, as well as olfactory bulb, all show transient elevations in $^3$[H] L-glutamate binding in neonatal and adolescent rats (Insel et al., Neurosci., 35: 31–43, 1990). Accordingly, NRF is an endogenous neuroprotective molecule, which accumulates in regions that would otherwise be especially vulnerable to excitatory amino acids during post-natal development.

The possible role of NRF as a neuroprotective molecule has important implications in the response of the adult brain to neuron damage. In adults, the anterior thalamic nuclei shows dense binding of both $^3$[H] glutamate and $^3$[H] glycine (O'Shea et al., Exp. Brain Res., 86: 652–662, 1991), which are excitatory amino acids thought to contribute to neuron damage. Surprisingly, though, the anterior thalamus has been identified as a "nonvulnerable" brain region during transient global ischemia (Globus et al., J. Neurochem., 57: 470–478, 1991). As discussed above, the anterior thalamus stains immunopositively for NRF. NRF activity in these regions thus may be implicated in protecting the anterior thalamus during transient global ischemia even though there are significant elevations in glutamate in this region following the ischemic insult (Globus et al., J. Neurochem., supra).

EXAMPLE 6

Preparation of NRPcc from Homogenates of Cerebral Cortex Tissue

Cerebral cortex tissue was excised from neonatal rat brains and homogenized at a ratio of 1 gm tissue in 4 ml phosphate-buffered saline (PBS) containing proteases (10 µl Pepstatin A; 12.5 µl phenylmethylsulfonyl fluoride (PMSF); 50 µl leupeptin). The homogenate was centrifuged at 1,000×g for 15 minutes at 40° C. to pellet nuclei and other cellular debris. The supernatant was collected and centrifuged at 100,000×g to separate membranes from the cytosolic fraction 40,000 rpm, Beckman Ti50rotor, 1 hour at 4° C.). The supernatant was collected into a separate container and the pellet was washed with 1 volume PBS and again centrifuged at 100,000×g as described above. The combined supernatants from the first and second centrifugations represented the cytosolic fraction from the tissue homogenate. NRF was purified from the cytosolic fraction by affinity purification with 8G6 antibodies, as described in Example 1.

NRF was purified from the membrane fraction of tissue homogenates by one of two procedures. In one procedure, the pellet from the 100,000×g centrifugation was dissolved in 4 volumes of a solution containing equal volumes of 2% SDS and PBS. The SDS-treated pellet was then subjected to centrifugation at 100,000×g, as described above. The supernatant was collected into a separate container, and the remaining pellet was re-suspended in PBS (1:4 tissue:buffer ratio) and again centrifuged at 100,000×g, as described above. The supernatants were combined and dialyzed against PBS containing 0.2% SDS overnight at 4° C. The dialyzate was then centrifuged at 100,000×g for 20 minutes at 4° C. to remove particulate material. The supernatant was concentrated by ultrafiltration. NRF was recovered from the concentrated fraction by affinity purification, as described in Example 1. This procedure recovers NRF polypeptide associated with the surfaces of the membranes or integrally embedded into the membranes.

In an alternative procedure, surface-bound NRF was isolated from the membrane fraction without dissolving the membranes in detergent. This procedure utilized a high-salt solution instead of detergent. Thus, instead of dissolving the membrane fraction in an SDS solution, the membranes were combined with 4 volumes of 0.8 M NaCl in PBS. The suspension was gently rocked for 1 hour at 4° C., then centrifuged at 100,000×g, as described above. The supernatant was removed to a separate container and the pellet was washed in 4 volumes PBS and re-centrifuged at 100,000×g, as described above. The supernatants were combined and dialyzed against 400 volumes PBS, with stirring overnight at 4° C. The dialyzate was subjected to centrifugation at 100,000×g for 20 minutes at 4° C. to remove particulate material. The supernatant was concentrated by ultrafiltration as described above. NRF was purified from the concentrated dialyzate by affinity purification as described in Example 1.

EXAMPLE 7

Preparation of HPLC-Purified NRF from Cytosolic Fractions of Cerebral Cortex Tissue Homogenates In Example 6, a simple method of preparing NRF from cytosolic and membrane fractions of cerebral cortex tissue homogenates containing NRF was described. In this example, an improved immunoaffinity purification procedure is described for isolating NRF from cytosolic fractions of cerebral cortex tissue homogenate, which also includes a column purification step (HPLC) for further purification of the factor.

A. Purification of NRF from Cerebral Cortex Cytosol

NRF was purified from the cytosolic fraction of the cerebral cortex of neonatal rats between 5 and 11 days of age. The cortex (including hippocampus) was removed from saline perfused rats and homogenized in ice cold 0.1 M Tris-HCl (1:2 wt/vol.) containing a cocktail of protease inhibitors. After an initial nuclear spin (700g), the supernatant was centrifuged at 100,000 g for 1 hr. This supernatant was passed through glass wool to remove floating lipid and then concentrated in Amicon® centrifugal concentrators (10 kD nominal MW cutoff) for Western blotting and affinity purification.

SDS-polyacrylamide gel electrophoresis followed by Western blotting of the cytosol revealed a prominent band at ~200–220 kDa. With the high protein loadings used to demonstrate this specific 8G6 antigen immunoreactivity, lighter less distinct bands sometimes appeared on the blots at ~60 kD and ~46 kD. These were determined to be IgG-like molecules in the cytosol (confirmed by blots of cytosolic proteins stained with an anti-rat IgG antibody). Control blots showed that these bands react with the goat anti-mouse IgG secondary antibody used to demonstrate 8G6 antigen immunoreactivity. Interestingly, the 55 kDa and 110 kDa bands that appeared in the CM affinity fraction (Example 1) were not present in this cytosolic fraction.

Affinity purification was accomplished in a 3 ml syringe loaded with 100–200 µl of protein A/G-agarose beads (Pierce Chemical Co.). The protein A/G was initially bound to 1–2 mg of rabbit antimouse IgG linker antibody (4–12 hrs at 4° C.) and then incubated overnight with 1–2 mls of ascites fluid containing the 8G6 antibody. Cross linking of the antibodies to the protein A/G was performed as described in Zacco et al. (1991, supra). The concentrated cytosol was circulated over the beads for 24 hrs at 4° C., after which the beads were washed first with 0.1% triton in 0.8M NaCl (40 min, to remove nonspecifically bound material), and then with PBS (40 min). The antigen was eluted with approximately 12 ml of 0.1 M glycine, pH 2.5 (presence of 8G6 antigen immunoreactivity confirmed initially by dot blots of 1 ml fractions) and the elution buffer was rapidly neutralized. The eluent was again concentrated with the Amicon concentrators and dialyzed overnight (dialysis membrane MW cutoff -12–14,000 D) against two changes of a 1000-fold excess of PBS. Protein concentration (against an albumin standard) was determined after the affinity purification and dialysis steps (see estimates below). This affinity-purified material is sometimes referred to herein as "cortex cytosolic affinity fraction of NRF."

Silver staining of the cortex cytosolic affinity fraction revealed a prominent band at ~200 kDa. This band was consistently recovered in nonreducing gels after the affinity purification step. IgG or IgG-like molecules (present in the cytosol, see above) or leached from the column were sometimes present as minor contaminants and appeared variably on the gels. Presumably, these bind (or rebind) nonspecifically to free protein A/G of the column and are eluted with the 8G6 antigen. These contaminants were eliminated with the final HPLC purification step (see below).

The reduced NRF protein was characterized on SDS gels. When the cortex cytosolic affinity fraction was treated with either β-mercaptoethanol or dithiothreitol, very little protein entered the resolving gel even with low percentage acrylamide gels, suggesting that NRF aggregates upon reduction. One possibility that was considered is that the molecule contains hydrophobic regions and reduction increases the ability of these regions to interact in adjacent molecules producing the aggregated protein.

Figure 4:
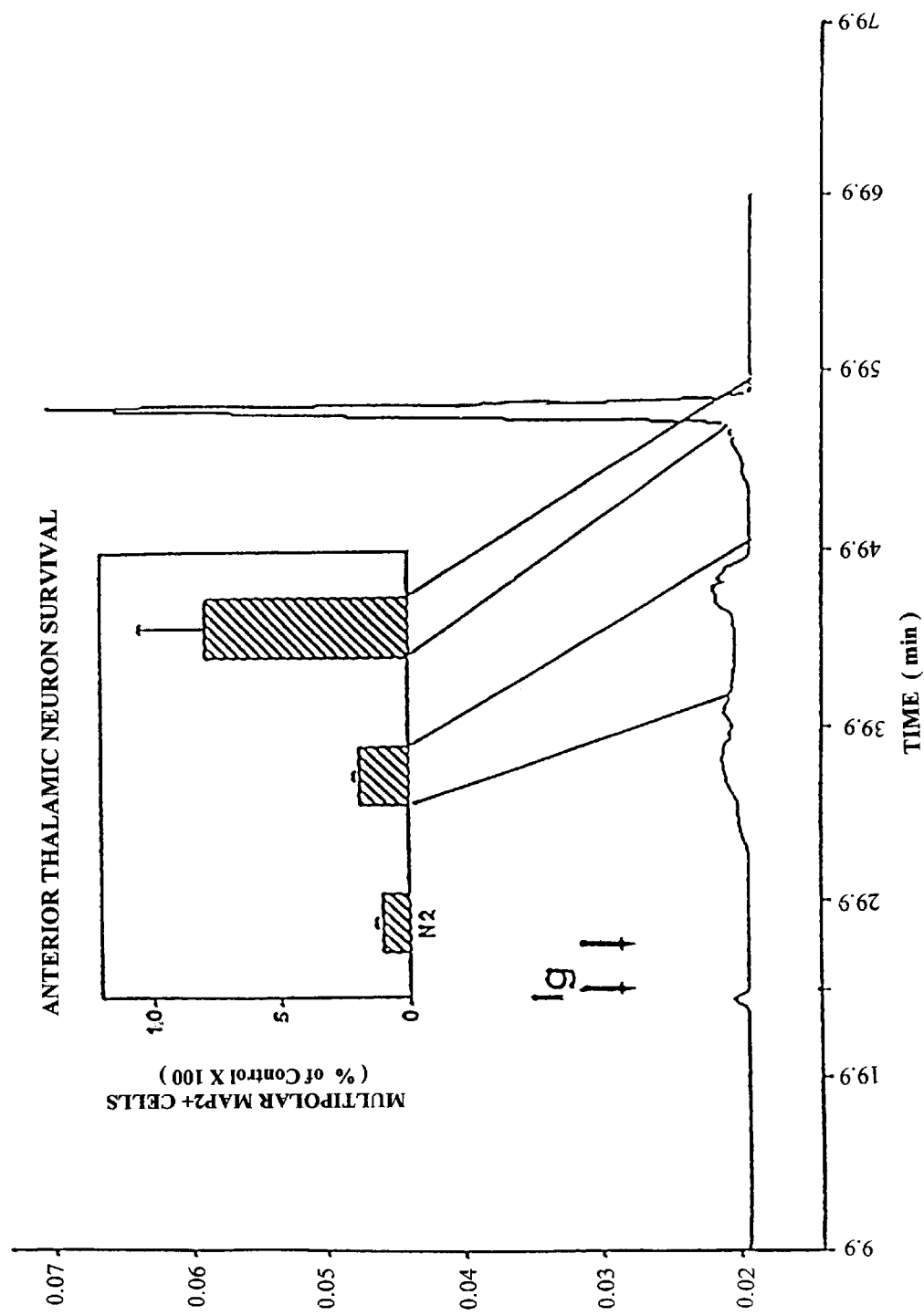
FIG. 4 is a typical HPLC purification profile of a cortex cytosolic affinity fraction containing NRF over a Superose 12 sizing column. Affinity-purified soluble brain fraction was run over the column with a two-step flow gradient (0.5 ml/min for 30 min, 0.2 ml/min for 30 min), to yield optimal separation of the NRF peak, which begins to elute at approximately 47 minutes. The positions of peaks for IgG and albumin standards run under identical conditions are indicated by the two downward-pointing vertical arrows. The inset histogram shows the results of testing the designated fractions with an in vitro bioassay, using anterior thalamic neurons. Fractions were concentrated and tested at 0.5 $\mu$g protein/ml. N2=N2 control; n=7 for all categories.

The hydrophobicity and/or shape of NRF was actually utilized in the final purification step. Affinity purified samples were run over a Superose 12 column using HPLC with a two-step flow gradient (0.5 ml/min for 30 min, 0.2 ml/min for 30 min). The running buffer was 10 mM HEPES, 10 mM NaCl, pH 7.0. NRF eluted as a single peak after 47 min, which is 30 minutes after the elution of IgG and albumin standards run under the same conditions (FIG. 4). This result was totally unexpected (larger molecules usually elute first with this column) but silver stained gels of the fraction containing this peak show the 200 kDa NRF band. Biological testing of this fraction showed that it is active in in vitro assays (see Example 8 below). The HPLC trace also showed some ill-defined low molecular weight elements eluting between 30 and 40 minutes. These are presumably either fragments of the IgG contaminants or of NRF, which have been cleaved by proteolytic enzymes during the affinity purification step (see above). Because these elements were the only possible contaminants of the NRF HPLC fraction, we tested a fraction containing them in the in vitro assay. This fraction is not effective. The protein eluted at 47 min from the Superose column is therefore homogeneous and biologically active. For biological testing, NRF-containing fractions from several runs were concentrated in the Amicon cells and stored as 100 μl aliquots at −70° C. prior to use. This material is sometimes referred to herein as "HPLC-purified NRF." Average yields of NRF from a single litter of rats (Av, size=12 pups) ranges from 10–18 μg after the affinity purification step and 3–6 μg after HPLC purification. These estimates are based on protein assays run against albumin standards.

B. Physical Characterization of HPLC-Purified NRF

The major protein component that was affinity purified from the cytosolic fraction of neonatal rat cerebral cortex was a 200–220 kDa polypeptide. The cortex cytosol affinity fraction was subjected to HPLC purification on a Superose 12 sizing column. The 200 kDa NRF polypeptide eluted from this column as a single peak starting at 47 minutes, under the HPLC conditions described hereinabove. The atypical elution profile of the polypeptide suggests that it may comprise a hydrophobic moiety, which interacts with the Superose 12 matrix to retard elution of the protein. However, as described above, the 200 kDa NRF polypeptide possesses a high specific activity for neurotrophic effects, and is believed to be the main active component defined herein as NRF.

As described in Example 1 above, the predominant band found in the CM affinity fraction was a 55 kDa band, and a possible dimeric form 110 kDa. Another polypeptide of ~200–220 kDa also appeared in the CM affinity fraction, but it was much less abundant than the lower molecular weight proteins. However, the 55 kDa and 110 kDa polypeptides were not present in the cytosolic fraction of cerebral cortex cells. Hence, the only polypeptide common to both the CM affinity fraction and the cerebral cortex cytosol was the polypeptide migrating at 200–220 kDa. In a procedure similar to that described above, the 200 kDa polypeptide was isolated from a conditioned medium of 5-day co-cultures of E14 occipital cortex and E14 diencephalon (CM). This 200 kDa protein has been shown to support thalamic neuron survival with high specific activity (see Example 8 below), at least 10–20-fold greater than that observed with the CM affinity fraction (0.1–0.5 μg/ml instead of 5 μg/ml, with survival at 4–8 fold over controls instead of 2 fold obtained with the CM affinity fraction). Accordingly, it was concluded that this species is the major neurotrophic component of the embryonic primordial CM.

NRF may be single polypeptide, or may comprise two or more polypeptides of lesser molecular weight. However, as described above, efforts to reduce the 200 kDa polypeptide have resulted in aggregation, rather than separation of any sub-components. Hence, if the 200 kDa NRF is composed of two or more sub-components, these components are tightly associated.

The above-described 200 kDa NRF protein was subjected to a tryptic digestion, and two peptide fragments of the digest were analyzed by amino acid sequencing, all according to standard methods. These are referred to hereinbelow as "Peptide No. 1" (Sequence I.D. No. 1) and "Peptide No. 2" (Sequence I.D. No. 2). Peptide No. 1 contains 21 amino acid residues and possesses a molecular mass of 2,219 Da. The sequence of Peptide No. 1 is as follows:

Asp-Leu-Tyr-Ala-Asn-Thr-Val-Leu-Ser-Gly-Gly-Thr-Thr-Met-Tyr-Pro-Gly-Ile-Ala-Asp-Arg

Peptide No. 2 contains 15 amino acid residues and has a molecular mass of 1,962 Da. The amino acid sequence of Peptide No. 2 is:

Tyr-Pro-Ile-Glu-His-Gly-Ile-Val-Thr-Asn-Trp-Asp-Asp-Met-Glu

The amino acid sequences of both Peptide No. 1 and Peptide No. 2 are identical to highly-conserved sequences found in several actins, including those of rat. For example, Peptide No. 1 has the same sequence as residues 293–313 of rat β-actin or residues 292–312 of rat γ-actin, cytoskeletal. Peptide No. 2 has the same sequence as residues 69–83 of rat β-actin. Both peptides correspond to loop-helix regions of the actin molecule, and are opposite each other and very similar in shape. Both loop regions appear to be in the nucleotide binding cleft of actin (see Kabsch et al., Nature, 6: 37–44, 1990).

Additionally, Peptide No. 2 is also identical to a tyrosine kinase hybrid that contains actin sequences (see Naharro et al., Science, 223: 63–66, 1984). Specifically, Peptide No. 2 corresponds to residues 91–106 of the tyrosine kinase "transforming protein" from feline sarcoma virus (strain Gardner-Rasheed).

Thus, NRF may be a hybrid protein, such as the aforementioned tyrosine kinase hybrid. Alternatively, NRF may be very tightly bound to one or more actin molecules (however, efforts to separate actin from the complex have not been successful). These actin sequences may serve to stabilize NRF once it is incorporated into the cells. Actin-stabilized NRF would be consistent with a model proposed recently for regulation of the N-methyl-D-aspartate (NMDA) channel (see Rosenmund & Westbrook, Neuron, 10: 805–814, 1993). In fact, there are several lines of evidence that NRF is indeed an actin-associated NMDA channel regulatory molecule as described by the above authors, among others. Furthermore, it appears that this regulatory factor is secreted or released so as to promote neuron survival. This evidence is summarized as follows: (1) NRF binds actin very tightly, or it contains actin sequences as part of a hybrid molecule; (2) NRF is distributed both intracellularly and extracellularly in regions of high glutamate binding during development so (a), it may be co-localized with NMDA receptors, and (b), it may be required as a protective element in regions where high levels of potentially toxic neurotransmitters (e.g., glutamate, NMDA) are present (this potential for protective action of extracellular NRF is further indicated by its binding to the surface of neurons in culture); (3) the concentration dependent activity of NRF is consistent with regulatory functions; (4) NRF has hydrophobic regions for interaction with the neuronal membrane where neurotransmitter receptors reside; and (5) the neuron-survival promoting activity of NRF is completely neutralized by high concentrations (5 mM) of glycine, another amino acid neurotransmitter that potentiates response of the NMDA receptor to its endogenous ligands, glutamate and NMDA (Mayer et al., Nature, 338:425–427, 1989). With regard to this last factor, the toxic effects of high concentrations of neurotransmitters like NMDA and glutamate are well known and have been associated with a variety of neurological diseases (see, e.g., Choi, Neuron 1: 623–634, 1988). In the experiments that reveal a glycine interaction, it is found, as expected, that NRF (affinity purified from cortex cytosol and tested at 1 $\mu$g/ml in the in vitro assay described in Example 8), produces a 700% ($\pm$270%) increase in anterior thalamic neuron survival over controls. This effect is entirely eliminated by the addition of 5mM glycine along with the factor. Since the site of action of glycine is at the NMDA receptor where there is actually a glycine binding site (Kemp et al., Proc. Nat. Acad. Sci. (USA) 856: 6547–6550, 1988), these data indicate that the site of action of NRF is also at this receptor. The effects of glycine on NRF activity may be due to a competitive or other antagonistic interaction, or simply due to the inability of NRF, at the concentration tested, to overcome the glycine-induced potentiation of NMDA responsiveness and associated toxicity.

To further examine the actin sequences in NRF, the following protolytic digestions were performed. Several digests of actin bands were initially made, both of monomeric actin and of aggregates (the latter being obtained with high protein loading). These were dissected from 10% polyacrylamide-SDS minigels, and then electrophoresed under non-reducing conditions. The dissected bands were placed in sample wells of a 20% SDS polyacrylamide gel; the sample wells were filled with an incubation buffer containing 2 mg/ml dithiothreitol (DTT). Following complete digestion with V8 protease (40 ng/$\mu$l, 30 minutes) and electrophoresis of the digest, the relative migration of the largest 8–10 active peptides was found to be highly reproducible in silver-stained gels. These actin digests were run side by side with proteolytic digests of NRF, which were prepared by dissection from a 10% non-reducing gel and treated in a manner identical to the actin digests.

The results of the NRF and actin proteolytic digests revealed at least seven bands that were found to be virtually identical to those obtained in other actin digests. The largest 5–6 peptides of these also appeared similar to those obtained by digestion of NRF. The smaller prominent pair of peptides in the actin digest appeared to be replaced with a single band in the NRF digest. These results are consistent with the aforementioned results suggesting that actin sequences are highly integrated into NRF, either very tightly bound or as part of a hybrid.

It should be noted that the 8G6 antibody does not cross-react with NGF or CNTF, and the molecular weight and chemical properties of NRF clearly distinguish it from such factors as BDNF, NT-3, or any of the interleukins with known neurotrophic effects.

EXAMPLE 8

In Vitro Assay to Determine Concentrations of HPLC-Purified NRF Effective to Promote Neurite Outgrowth and Survival of Selected Neuron Populations To determine concentrations of HPLC-purified NRF from cerebral cortex (described in Example 7) effective to promote survival and neurite outgrowth of neurons in vitro, we developed an in vitro assay that measures the survival of neonatal thalamic neurons. This improved in vitro assay utilizes cells, the majority of which are axotomized during harvesting, which most closely corresponds to cells measured in the in vivo models described herein, where lesions are made in neonatal rats. In addition, dissections of neonatal animals can be more accurately centered on thalamic regions of interest, as compared to embryonic animals, wherein accurate dissections are often difficult. Additionally, the assays described hereinbelow use two preplating steps, which yield highly purified neuronal cultures.

Tissue was harvested from the thalamus of postnatal day (PND) 1-PND 3 animals. For the anterior thalamus, the dorsal half of the rostral 0.5 mm of the diencephalon was dissected. This region includes the habenula, the anterior nuclei (AN), and the rostral part of the lateral dorsal nucleus (LD). The habenula was removed with further dissection. For the posterolateral thalamus, the caudal 0.5 mm of the diencephalon (just in front of the optic tectum) was dissected and the dorsal lateral one-third of this slice was collected. This region includes primarily the dorsal lateral geniculate nucleus (dLGN), but also parts of the ventral lateral geniculate nucleus (vLGN), the lateral posterior nucleus, and a small lateral-most segment of the ventrobasal nucleus (VB).

After micro-dissection to remove meninges and blood vessels, the cells were dissociated and plated on tissue culture plastic in DMEM-F12 containing 10% fetal bovine serum. After 45 min–1 hr, the cultures were examined for adherent cells while tapping the dish on the microscope stage. Non-adherent cells were replated in the same nutrient mix and harvested again after another 45 min. The medium was collected and centrifuged at 200 g for 10 min. The cells were counted and incubated in defined serum-free medium (N2, made from DMEM with L-glutamine added; Bottenstein, 1985, supra) in 0.38$\times$1.17 cm$^2$ plastic wells with polylysine. This medium was supplemented with 0.2% glutamine. Each well was plated with 4,000–10,000 cells. Staining of the cultures with either a MAP2 or GFAP antibody after terminating the cultures revealed 95–99% of surviving cells were neurons.

Initially, the cells were incubated in 90 $\mu$l of N2 medium. After 2 hrs, 10 $\mu$l of the cortex cytosol affinity fraction containing NRF (Example 7) or specific fractions collected after gel filtration by HPLC containing NRF, or dialysis buffer controls (all diluted if necessary to required final concentrations with N2) were added to the cultures. The cultures were terminated after another 22 hrs, fixed, treated with 0.1% triton X-100, and stained with an antibody against MAP2 (a neuron specific marker). MAP2+ neurons bearing multiple MAP2+ processes (>2) were counted in 8 systematically defined fields at 200× magnification. At optimal concentrations of cortex cytosol affinity fraction or HPLC-purified NRF, absolute numbers of such cells surviving and growing multiple MAP2+ processes in the cultures were between 1000–3,000/well depending on the age the cells are originally harvested (PND1>PND2>PND3).

Figure 5:
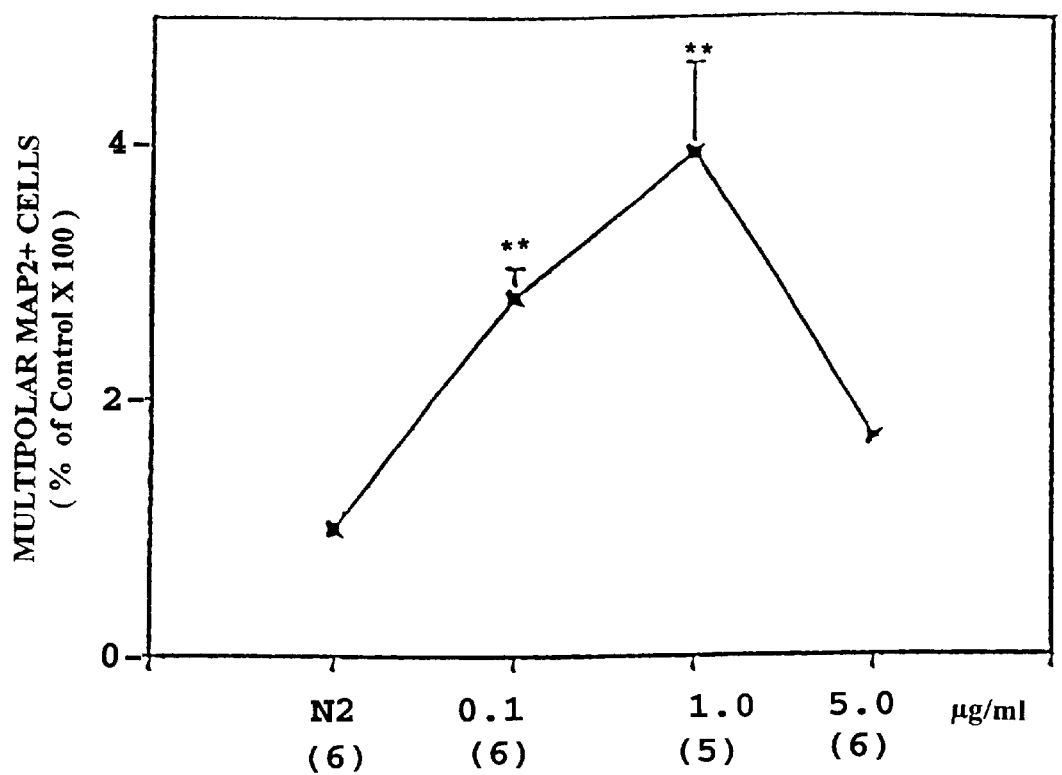
FIG. 5 is a graph showing the effects of adding different concentrations of the cortex cytosolic affinity fraction containing NRF to cultures of anterior thalamic neurons harvested on postnatal day 2. N2=N2 control; various concentrations of the neuronal cytosolic fraction (0.1, 1.0 and 5.0 $\mu$g/ml, respectively) were added 2 hours after plating the cells. The graph shows the number of MAP2+ cells at the three different concentrations of NRF, expressed as a percentage of N2 control. The number of cultures for each concentration are in parentheses and statistical comparisons are by the Mann-Whitney $\underline{U}$ test.
Figure 6A:
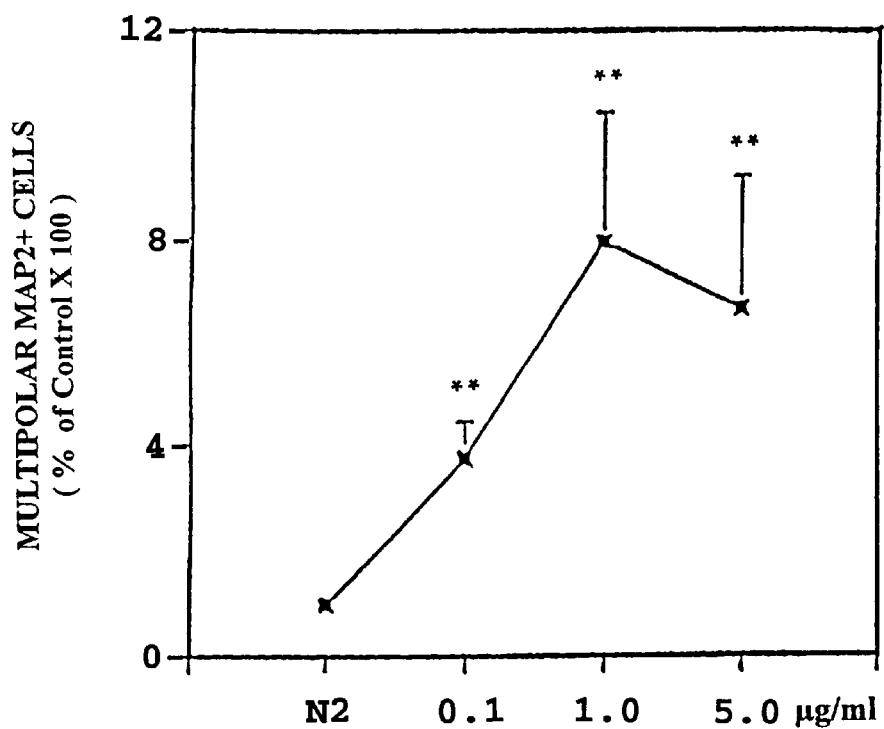
FIGS. 6A–B is a pair of graphs showing the effects of adding HPLC-purified NRF to anterior (FIG. 6A) or posterolateral (FIG. 6B) thalamic neurons harvested on postnatal Day 2. Data are from 24-hour cultures in which three different concentrations (0.1, 0.5 and 1.0 $\mu$g/ml) of HPLC-purified NRF were added 2 hours after final plating of the neurons. The number of multipolar MAP2+ cells at the three different concentrations is expressed at a concentration of N2 control. n=7 for all categories and statistical comparisons are by the Mann-Whitney $\underline{U}$ test.

The effect of treating the cultures with appropriate concentrations of either the cortex cytosol affinity fraction or the HPLC-purified NRF is striking. In cultures of anterior thalamic neurons (FIGS. 5, 6), a 4–8 fold increase in the numbers of multipolar Map2+ cells was found when the cultures receive NRF compared to the control cultures (N2 alone, non-NRF fractions from HPLC). The most obvious effect of NRF is to increase the number of neurons with multiple MAP2+ processes and the intensity of MAP2 staining in the cell body. High concentrations of NRF give effects similar to N2 controls in that there are fewer surviving neurons and less outgrowth. Although reduced in number, the neurons exposed to these higher concentrations may still show increased intensity of MAP2 staining, suggesting the cells may be viable but just not growing. Comparing the effects of the cortex cytosol affinity fraction containing NFR with HPLC-purified NRF indicates that similar concentrations are effective but there is increased trophic activity (8 fold versus 4 fold increases over N2 controls) with the HPLC purified NRF, at least for neurons in the anterior thalamus (compare FIGS. 5 and 6A).

Figure 6B:
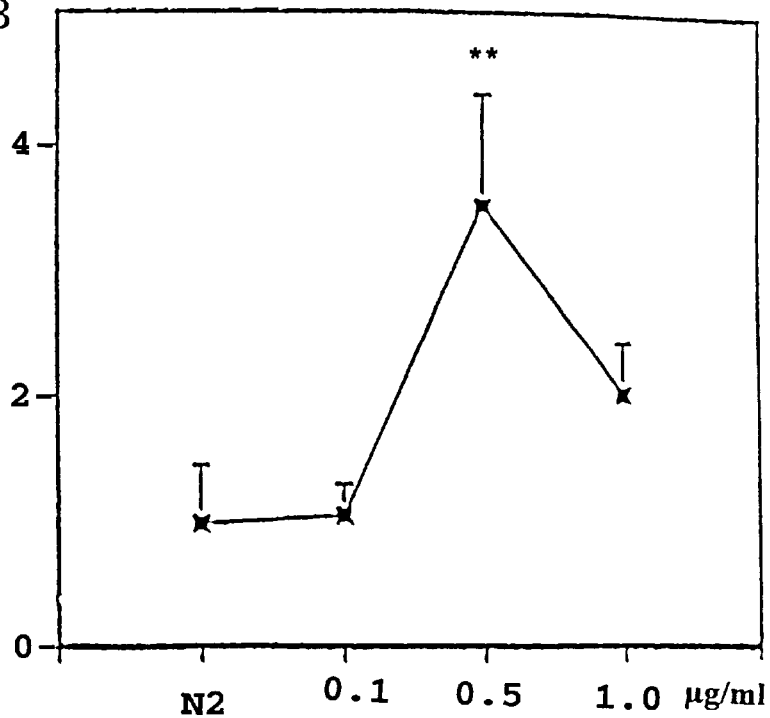

Posterolateral thalamic neuron cultures also respond to NRF. There is overall lower specific activity of the protein (4-fold increases in neurite outgrowth and neuron survival at the optimal concentration) and the concentration curve is sharper (FIG. 6B). These differences may reflect intrinsic differences in the concentration requirements of anterior versus posterior thalamic neurons for maximal responsiveness. It may also be that these two regions develop at different rates and so their sensitivity to NRF may also develop differently. Furthermore, diminished support of these neuronal populations with increased concentration of NRF is reminiscent of the results obtained with the CM affinity fraction in vivo (also on posterolateral thalamic neurons, i.e., those of the dLGN, see Examples 3 and 4 above), and those obtained in vitro with other neurotrophic molecules such as NGF and bFGF.

EXAMPLE 9

Preparation of NRFrb from the Culture Medium of Human Retinoblastoma Cells

The size and unusual chemical properties of NRF have enabled purification of a human form of NRF from the medium of the Y9 human retinoblastoma cell line, obtained from the American Type Culture Collection. These kinds of cells form a common tumor of childhood and are suggested to consist of neuroblasts with the potential to become either photoreceptors or Muller cells. Retinoblastoma cells were selected as a possible source of human NRF because of the dense immunostaining observed with the 8G6 antibody in the synaptic layers of the neonatal rat retina, including the developing outer plexiform layer where the photoreceptors make connections. Immunostaining with the 8G6 antibody has also been observed in the cellular layers of the retina.

The human retinoblastoma NRFrb is weakly immunoreactive to the 8G6 antibody (raised against rat NRF), but can be purified from serum-free medium by ultrafiltration, dialysis and repeated HPLC gel filtration, according to methods described herein for purification of NRF from the cytosol of rat cortical neurons. Such purification yields a large polypeptide or complex of polypeptide approximately 200 kDa in molecular weight.

Figure 7:
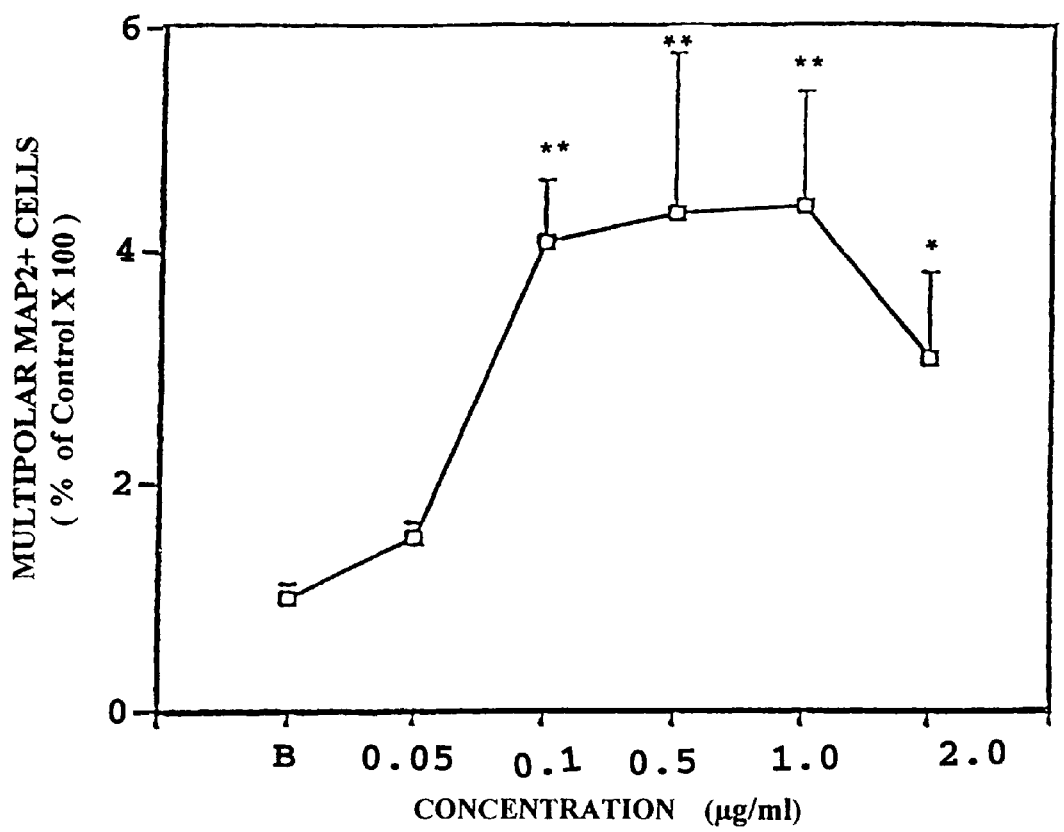
FIG. 7 shows survival of multipolar MAP2+ cells after adding various concentrations of the NRF derived from cultured human Y9 retinoblastoma cells, NRFrb. Two hours after initial plating of the cells, different concentrations of the retinoblastoma-derived protein were added to the cultures. B=elution buffer control; n=7 for all categories. Statistical comparisons are to the buffer control by the Mann-Whitney $\underline{U}$ test.

The human retinoblastoma NRFrb was tested in the in vitro assay described in Example 7. The human protein was found to support the survival of rat thalamic neurons in a concentration-dependent manner. FIG. 7 shows a graph of the survival of multipolar MAP2+ cells after adding various concentrations of the human retinoblastoma NRFrb. As can be seen from FIG. 7, the human protein was optimally effective between 0.1–1.0 μg/ml, similar to the effective concentration range of HPLC-purified NRF from rat cortical cytosol.

EXAMPLE 10

Purification of the Cytoprotective Protein Component of NRF. NRFSCI

As described in Example 7, NRF exhibited unusual behavior on Superose 12 HPLC columns. Specifically, it was retained on the column much longer than would be predicted from its size. One explanation for such behavior would be the existence of a large charge on NRF, or a component thereof. The purification of NRF was modified to explore this hypothesis. As a result, the NRF complex was found to comprise an acidic protein, formally referred to as the "cytoprotective protein" (CPP), now designated NRF subcomponent I, NRFSCI. NRFSCI possesses cytoprotective activity in vitro and in vivo. Isolation of this protein was accomplished by affinity purification of cytosolic or secreted actin, followed by acid separation on a Superose 12 column. This example sets forth protocols for purifying NRFSCI from various sources, and describes the characteristics of the NRFSCI.

A. Purification of NRFSCI

NRFSCI has been purified from the soluble fraction of rat brain cell homogenates or medium conditioned by cell lines having neural properties (these include mouse hippocampal neuron (HN) 33.1 cells, as described by Lee et al. J. Neurosci. 10: 1779–1787, 1990; and human Y79 retinoblastoma cells, as described in Example 9). Although other cell lines have yet to be tested, it is believed that most cells will contain the NRFSCI molecule in association with actin-containing cytoskeletal complexes.

When conditioned culture medium was used as the starting material, the cultured cells were exposed to 0.1% $H_2O_2$ for 30 minutes, a severe oxidative stress that causes extrusion of cytoskeletal proteins and lysis of many of the cells. The medium was collected, filtered through a 0.22 μg bottle filter then concentrated 200× with Amicon centrifugal concentrators having a 10 kDa molecular weight cutoff.

When brain homogenates were used as the starting material, the homogenates were prepared from the cerebral cortex of rats after perfusion of the animals with phosphate-buffered saline (PBS). The tissue was homogenized in ice cold PBS (1:4 wt:vol) spiked with protease inhibitors (PMSF, 50 μg/ml; leupeptin, 1 μg/ml; pepstatin, 1 μg/ml). The homogenate was centrifuged at 200g for 20 minutes, after which the supernatant was collected and spun at 100,000 g for one hour. The supernatant from the high speed spin was passed through glass wool to remove floating lipid, then concentrated to 5 ml with the 10 kDa Amicon concentrators.

The concentrated culture medium or soluble brain fraction was loaded onto an actin affinity column, which was prepared by cross-linking 1 μl of a rabbit polyclonal antibody (anti-chicken muscle actin, Sigma Immunochemicals) to protein A/G beads (Pierce) according to procedures outlined by Zacco et al., J. Neurosci. 10: 73–90 (1990). Actin, or complexes comprising actin epitopes, became bound to the actin affinity column. The actin or actin-containing complexes were eluted from the column with 2.5 mM glycine (pH 2.5) and rapidly neutralized with 1 M Tris-HCl (pH 9.0). Fractions from the actin affinity column (1 ml) were collected and tested for protein content by measuring absorbance at 280 nm. The protein-containing fractions were pooled and dialyzed overnight against two changes of 1000-fold excess of PBS (0.1 M $NaPO_4$, 0.9% NaCl) which had been diluted so as to give a final concentration of 1× after concentrating the dialyzed protein sample to 200 μl.

The dialyzed sample was next loaded onto a Superose 12 column (Pharmacia). However, instead of eluting proteins with a buffered solution, as described in Example 7, the column was run with 0.05 M HCl (pH 1.5) for 90 minutes at 0.3 ml/min by HPLC (Peptide Mapping System, Perkin Elmer, Norwalk, Conn.). This acid elution procedure yielded a prominent protein peak ($A_{280}$, $A_{max}$=225 nm) after 70 minutes or 21 ml of the HCl elution solution (see FIG. 8). The acid-eluted protein was not soluble actin, which was found to adhere to the column under acidic conditions. The column was washed with 100 ml filtered water, then 20 ml of 0.1 M NaOH for 30 minutes. The NaOH treatment resulted in elution of a much larger peak (5–15 fold greater $A_{280}$ then the acid-eluted peak), which was confirmed to be enriched with actin species by SDS-PAGE, Coomassie Blue Staining and Western Blot analysis with an anti-actin antibody.

In a preferred embodiment of the invention, the acid-eluted protein is further purified by native polyacrylamide gel electrophoresis under non-reducing conditions. The fastest-migrating band on a native gel was found to contain the NRFSCI, and was eluted from the gels. Elution of the protein from polyacrylamide gels was accomplished by pulverizing the gel piece containing the protein band in 500 μl of PBS and then dialyzing against 500 ml of PBS through 3 kDa cutoff dialysis membrane for 24 hrs. This was followed by dialysis against 500 ml of 10 mM $NaPO_4$ for an additional 24 hours. The dialyzed protein solution was stored at −70° C. for biological testing.

B. Physical Characterization of Acid-Eluted NRFSCI

Figure 8:
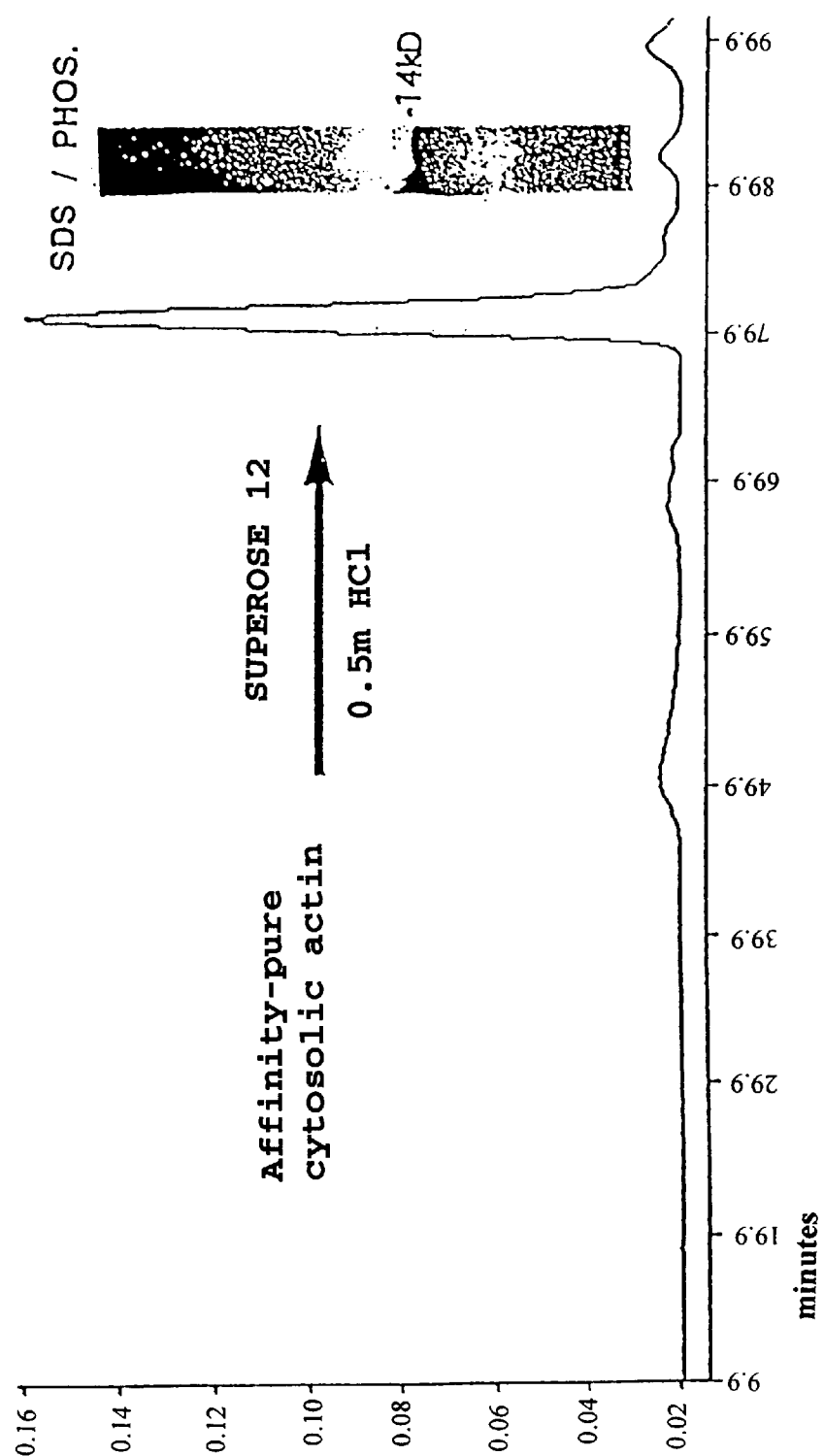
FIG. 8 shows the elution profile of affinity-purified cytosolic actin or actin-containing proteins from a Superose 12 HPLC column run with 50 mM HCl. The X axis represents elution time in minutes and the Y axis represents absorbance at 280 nm. Also shown in the inset is the pooled protein peak from the HPLC acid elution, subjected to SDS-PAGE with 100 mM sodium phosphate (pH 7.2) as the gel sample running buffer. Under these conditions, the acidic protein NRFSCI migrates with apparent molecular weight under 14 kDa, as indicated.

The acid-eluted protein from the Superose 12 column was collected and electrophoresed under non-reducing conditions for 1.5–2 hours on a precast 4–20% polyacrylamide gradient gel or a non-gradient 15% gel (Biorad, Melville, N.Y.) made without SDS. SDS was added in low concentration to both sample and running buffer (sample buffer was 0.5% SDS in 100 mM Tris, pH 6.8; running buffer was 0.1% SDS in 150 mM Tris/35 mM glycine, pH 8.4). Electrophoresis of the acid-eluted fraction resulted in a resolution of a prominent protein band between 14 and 21 kDa, $NRFSCI_{14-21}$ (centered at about 17 kDa) and another at about 66–69 kDa. It appears that these two bands are related, although the higher molecular weight band was found to be resistant to total reduction by standard disulfide reducing agents. Nevertheless, when $NRFSCI_{14-21}$ protein was eluted from the gels (see below) and run again by SDS-PAGE under non-reducing conditions, the 69 kDa band reappeared. The 14–21 kDa band was intensified by pre-treatment with 2 mM N-ethyl maleimide and addition of 2 mg/ml dithiothreitol to the sample; however, the 66–69 kDa band still appeared and may also have been intensified. In addition, aggregation was least if the HPLC acid fraction was run on gels with 100 mM sodium phosphate (pH 7.2) as the gel sample and running buffer. Under these conditions, the protein did not aggregate, but migrated with an apparent molecular weight below 14 kDa (FIG. 8). It is possible that the highly alkaline conditions that develop in these gels destroy the sulfhydryls and disulfides present in the protein aggregates (it should be noted however that sequence data is so far only suggestive of the presence of cysteine, see below).

The acid-eluted NRFSCI exhibited additional variations in size and aggregation when subjected to different SDS-PAGE conditions. For example, treatment of the 14–21 kDa band with SDS and DTT, but without boiling, resulted in the disappearance of the 14–21 kDa band and appearance of a smaller band migrating at about 2.5 kDa. If the SDS/DTT-treated sample was boiled, the 2.5 kDa band disappeared and the 14–21 kDa band reappeared on the gel. The 2.5 kDa band possesses the same amino-terminal amino acid sequence as the 14–21 kDa band (see below) and is set forth herein as Sequence I.D. No. 3. These results indicate that the 14–21 kDa band itself may be comprised of subunits that can aggregate under certain conditions. Thus, the acid-eluted NRFSCI appears to exhibit the ability to aggregate from a very small component (2.5 kDa) to a relatively large component (66–69 kDa).

The protein bands were viewed with either Coomassie Blue, silver, or the Protein Quick Stain (Zoion, Newton, Mass.). When the latter was used, the protein was not fixed and the band could be excised and eluted for biological testing or for further electrophoretic analysis as described above. Also, both the 14–21 and 66–69 kDa bands appeared atypical with this technique. They were dark purple instead of white against a purple background, indicating that these species have exaggerated the purple redox product instead of inhibiting it, as expected for most proteins. These data provide another indication that the acid-eluted protein contain reactive sulfhydryls and therefore possesses reducing properties.

C. Amino Acid Sequence Analysis and Western Analysis

Proteins were transferred from the gel for amino acid sequencing or Western analysis in a Tris/glycine buffer containing 10% methanol and 0.01% SDS. Transfer was for 2 hours at a constant current of 250 mA. N-terminal or internal sequences (the latter obtained after tryptic digestion of the protein gel-eluted) were determined from amido black-stained blots with a Hewlett-Packard G1005A Sequencer. Resulting sequences were compared to known sequences in a non-redundant composite protein database after accessing the BLAST program provided by the National Institutes of Health. For Western analysis, nitrocellulose blots were incubated with a polyclonal anti-actin antibody (Sigma), an appropriate secondary antibody conjugated to horseradish peroxidase, and finally developed with 4-chloronapthol or by chemiluminescence. The Western Blots and companion Coomassie Blue-Stained gels confirmed that the NRFSCI is purified primarily from cytosolic actin containing peptides.

Amino terminus sequence obtained for the human NFR-SCIrb (obtained from Y9 retinoblastoma cells), determined after application of the above procedures, is as follows (Sequence I.D. No. 3):

$Xaa_1$-Asp-Pro-Glu-Ala-Ala-Ser-Ala-Pro-Gly-Ser-Gly-Asn-Pro-$Xaa_2$-His-Glu-Ala-Ser-Ala-Ala-Gln-$Xaa_3$-Glu-Asn-Ala-Gly-$Xaa_4$-Asp-Pro. In Sequence I.D. No. 3, $Xaa_2$ is probably Cys and $Xaa_4$ is probably Glu.

A search of the database revealed no strong homologies with any vertebrate proteins, although at the N-terminus there is partial alignment (77% homology of residues 1–13)

with a 13 amino acid fragment reported for an antigen isolated from β-hemolytic streptococci, (Yoshizawa, et al., J. Immunol. 148: 3110–3116 1992). Although the data reported by Yoshizawa wt al. indicate that the fragment may also be associated with cytosolic actin, no cytoprotective activity was reported for the fragment or at any stage of purification of the protein species claimed to be associated with it.

Analysis of the sequence by GenePro software indicates that the amino-terminal portion of the NFRSCI is hydrophilic and very acidic (negatively charged at physiological pH). The sequence represented by amino acids 16–30 (when searched alone) has no known homology.

EXAMPLE 11

Cytoprotective Effects of NRFSCI in vitro and in vivo

The HPLC acid fraction containing the NRFSCI, as well as the gel-purified band itself (from both mouse and human sources), have cytoprotective effects in vitro and in vivo. The principal in vitro assay that is applied in experiments described in this example uses the hippocampal cell line (HN 33.1) plated in a 100 μl protein-free medium (DMEM) on plastic microwells. The cells attach and grow neurites in a few hours and their vitality can be tested at any time by application of MTT (Thiazol Blue, Sigma). Large numbers of these cells are killed by two changes of medium 30 minutes apart.

Figure 9:
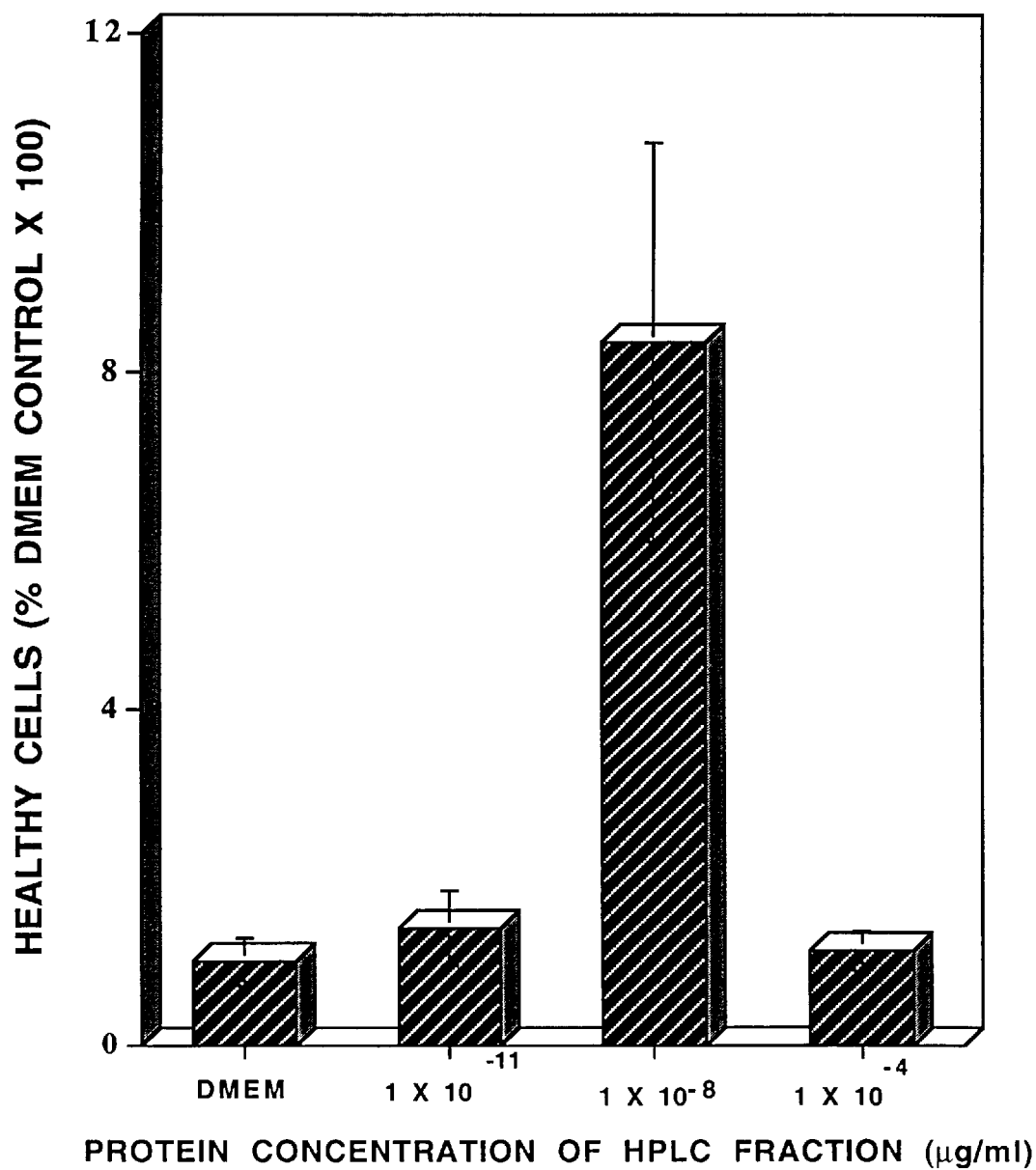
FIG. 9 is a histogram comparing the effects of various medium changes on the survival of HN 33.1 cells plated in a 100 $\mu$l protein-free medium (DMEM) on plastic microwells. Cell vitality (Y axis) was tested by application of MPT (Thizol Blue, Sigma Chemical Co.). Large numbers of the these cells are killed by two changes of medium, thirty minutes apart. In the histogram, the second medium change comprised removing the conditioned medium and replacing the medium with DMEM or different concentrations of NRFSCI$_{14-21}$ purified from conditioned medium of cultured HN 33.1 cells and subjected to HPLC acid elution. X-axis represents protein concentration ($\mu$g/ml), Y-axis represents the number of viable cells remaining in the culture, expressed as a percentage of a control treatment (cells receiving no NRFSCI$_{14-21}$); T-bar=range among independent experimental cultures.

It has been suggested that accumulation of glutamate contributes to cell death following medium change (Driscoll et al. J. Neurochem 61: 1795–1800, 1993). FIG. 9 shows that there was significant rescue of the HN cells if, at the time of the second medium change, the 30 minute conditioned medium was removed and then simply put back in the same cultures, or transferred to parallel cultures for the second medium change. In the control cultures, unconditioned DMEM at the same temperature and pH was used instead of the 30 minute conditioned medium. These results suggest that the conditioned medium has cytoprotective properties which could be present in the secretions of the living HN cells and/or the lysed products of degenerating cells. The evidence presented below suggests that NRFSCI, which is closely associated with soluble intracellular and extracellular actin, participates in that protective response.

Figure 10:
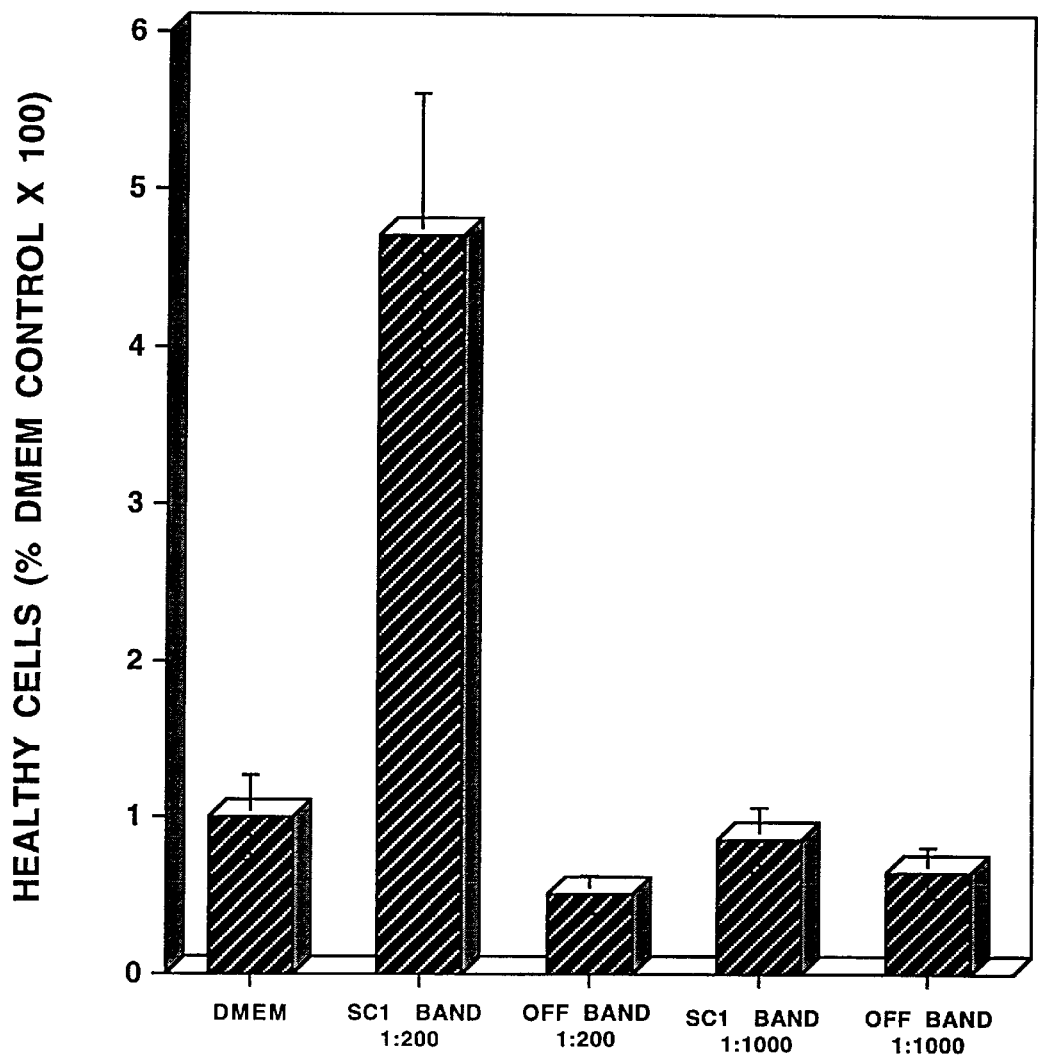
FIG. 10 is a histogram showing the effect of different dilutions of the NRFSCI$_{14-21}$ eluted from the 14–21 kDa polyacrylamide gel band and subjected to repeated dialysis. On the X-axis, "NRFSCI$_{14-21}$" represents protein concentration expressed as a dilution of a 500 $\mu$l gel eluent solution, "Off Band" represents identically prepared eluent from the same gel, but outside the 14–21 kDa band, "DMEM" represents the DMEM control. Y-axis represents the number of viable cells remaining in the culture, expressed as a percentage of a control treatment (cells receiving no NRFSC$_{14-21}$); T-bar=range among independent experimental cultures.

Both the HPLC acid fraction containing the NRFSCI and the gel-eluted NRFSCI$_{14-21}$ protein band are cytoprotective. This was seen clearly in the HN cell line assay described above, where significant cell rescue was obtained when the second (30 minutes) medium change was supplemented with very small amounts of the acid HPLC purified protein in DMEM (FIG. 9). Although concentration estimates are expected to be imprecise because they are based on assays using BSA standards, the results suggest that the NRFSCI is active in sub-femtomolar amounts, assuming a molecular weight of around 10,000 Daltons ($10^{-8}$ μg/ml=$10^{-11}$ g/L/$10^4$ g/mole=$1\times10^{-15}$ M/L). Even if these estimates are incorrect by as much as a few orders of magnitude, the data indicate high affinity interactions of the NRFSCI with its substrate. Estimates of protein concentrations obtained when the NRFSCI band is eluted from the acrylamide gel have been difficult because amounts are too small to measure accurately. In the experiment shown in FIG. 10, a 1:200 dilution of the protein gel-eluent solution (which had a starting volume of 500 μl for about 1×3mm gel strip) affords significant protection to the HN cells (On Band). Similar dilutions of control gel pieces (Off Band) were also tested, and no effect was found.

The gel-eluted NRFSCI$_{14-21}$ protein was found to be most effective when added to the cells at pH 6.8 rather than 7.4. While the cultures attained the higher more physiological pH after 24 hours, it is possible that the mildly acidic conditions initially are required to activate NRFSCI, which may be most effective in its reduced form. In other words, slightly acidic conditions (such as those which occur in the brain after various insults) may favor the reduced form of the NRFSCI or may facilitate release of the peptide from cytoskeletal elements.

In vivo testing of the cytoprotective properties of the NRFSCI$_{14-21}$ was performed on rats with large suction lesions of the posterior pole of the cerebral cortex, as described in Example 4. The lesions include all cellular layers of the cortex but spare much of the underlying white matter. Similar lesions were made in both cortices except one side was treated with the NRFSCI$_{14-21}$ while the other received vehicle (DMEM). As expected, effective concentrations for the in vivo studies were much higher than for the in vitro experiments. In a total of 10 animals, the HPLC acid fraction containing the NRFSCI$_{14-21}$ (n=6) was tested at concentrations between 0.02–0.5 μg/ml while the peptide band gel eluent (N=4) was diluted 1:2 or 1:3. Degenerative changes in surviving cortical areas were determined 1 week after the lesion by immunocytochemistry of tissue sections using antibodies to microtubule associated protein-2 (MAP-2). MAP-2 has been applied in a number of studies of neuron degeneration (e.g., ischemic injury, anoxia, hyperammonemia, uremia) and is a sensitive early indicator of tissue destruction in the central nervous system (see reviews by Johnson and Jope J. Neurosci. Res. 33: 505–512, 1992; Matesic and Lin, J. Neurochem. 63: 1012–1020, 1994).

Figure 11:
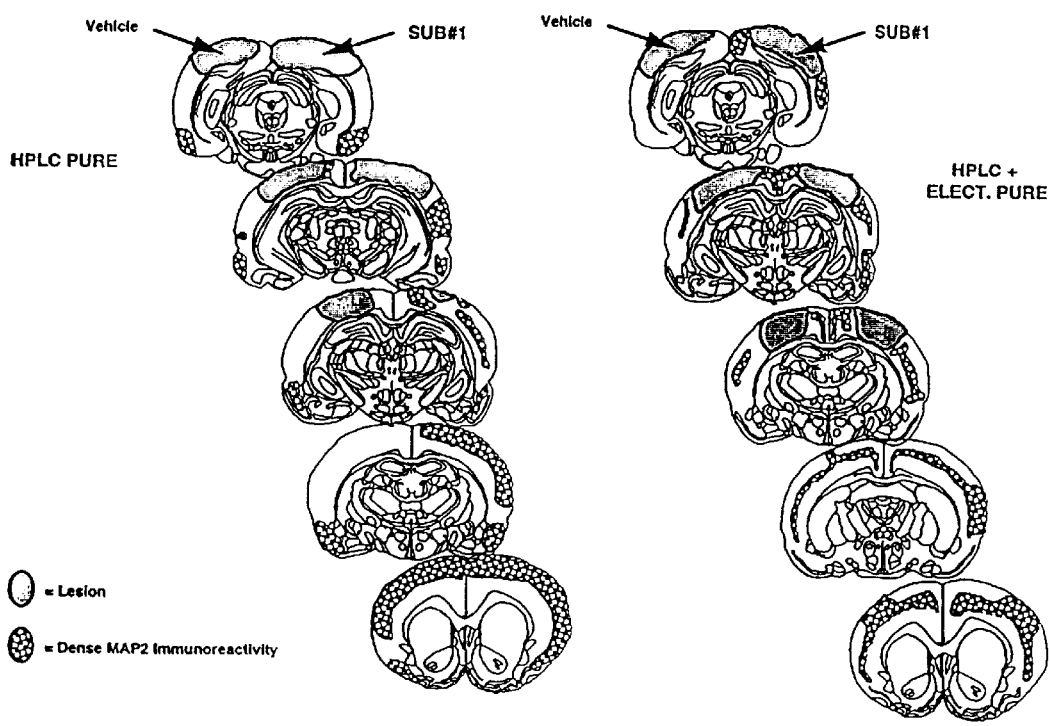
FIG. 11 is a diagrammatic depiction of results from immunostaining with antibodies to the MAP-2 protein in surviving cerebral cortex after cortical lesions and treatment with NRFSC$_{14-21}$ protein. MAP-2 is a sensitive indicator of neuronal damage. From top to bottom, the diagrams represent serial sections, from rear to front of the cerebral cortex surrounding posterior cortex lesions in adult rats. Areas circled with bold black lines represent areas of the lesion; stippled areas represent regions of dense MAP-2 immunoreactivity. Diagrams of serial sections on the left side of the figure are the results of treatment with the pooled protein fraction of NRFSCI$_{14-21}$ from acidic HPLC elution on Superose 12; serial sections on the right side of the figure represent treatment with NRFSCI$_{14-21}$ that was further purified by SDS-PAGE and eluted from the polyacrylamide gel. In both serial sections, vehicle was added to the lesion on the left hemisphere, while the NRFSCI$_{14-21}$ was added to the lesion on the right hemisphere.

The result of posterior cortex lesions in adult rats is a loss of dense MAP-2 immunoreactivity (i.e., immunoreactivity that is at least 3× background staining) in a region several hundreds of microns adjacent to the lesion. In the examples shown in FIG. 11, this loss was seen clearly on the side of the brain where vehicle was applied to the lesion cavity and indicates a loss of cytoskeletel integrity in neurons adjacent to the lesions, as well as exaggerated neuronal death in the remaining tissue of this hemisphere. By contrast, large regions of MAP-2 staining were rescued in the hemisphere treated with the NRFSCI$_{14-21}$, suggesting that NRFSCI$_{14-21}$ protects neurons vulnerable to degenerative changes over a relatively large area of the cerebral cortex. Eight of the 10 animals have shown this rescue effect.

NRFSCI also exerts a protective effect on non-neuronal cells. This effect was demonstrated on cardiac muscle cells. Adult rat cardiac muscle cells were dissociated with trypsin/collagenase-dispase solution and plated on poly-l-lysine in serum free medium (DMEM). The medium was changed once to induce oxidative stress in the cells, and thereafter replaced with either DMEM or acid HPLC-eluted NRFSCI ($1\times10^{-5}$ μg/ml). Estimates from direct counts of surviving muscle cells indicated a significant increase in survival of NRFSCI-treated cells, as compared with the DMEM control.

EXAMPLE 12

The mechanisms that govern anatomical repair processes in the nervous system are not well understood because until relatively recently it was assumed that these processes were very limited. The discovery of morphological plasticity in the brain, especially after injury, led to renewed interest in recovery of function and strategies to enhance recovery, including CNS transplantation. An important aspect of any repair strategy is the response of glia cells to lesions. The monocyte-derived microglia and brain macrophages (BMOs) have been of considerable interest because they are a source of powerful growth-promoting as well as highly toxic substances, and because both cell types are prominent at lesion sites (Milligan, et al., 1991, J. Comp. Neurol. 314:125–146). In the case of CNS microglia and BMOs, it is now generally conceded that they have a destructive influence after CNS damage (Banati, et al, 1993; Guilian, 1990). Initially, BMOs and microglia respond vigorously to cerebral cortex lesions. Lesions in infant rats, where normally there is a large transient population of resident BMOs along with endogenous microglia, are especially destructive, resulting in rapid and efficient neuron degeneration and removal. (Milligan, et al, 1991, J. Comp. Neurol. 314:125–146).

Monocyte-derived cells can exacerbate CNS lesions through the production of cytotoxins such as reactive oxygen intermediates, glutamate, or nitric oxide (Chao, et al., 1992, J. Immunol. 149:2736–2741; Colton and Gilbert, 1987, FEBS Letts 223:284–288; Piani, et al., 1991, Neurosci. Lett. 133:159–162). In addition, in vivo activation of microglia/BMOs leads to production of unidentified neurotoxic substances identified in vitro (Guilian et al., J. Immuno. Immunopharmacol. 10:15–21 1993). Treatment of retinae with a tripeptide inhibitor of macrophages (unfortunately, sometimes called MIF), keeps a small percentage of axotomized retinal ganglion cells alive if the cut axons are also presented with a peripheral nerve graft (Thanos and Mey, 1995, J. Neurosci. 15(2):1057–1079). It should be noted that one hypothesis underlying the proposed role of NRF is that NO production, for example, might be limited after treatment of brain wounds with NRF because of binding of the NRF to Migration Inhibitory Factor (the original MIF), a cytokine that stimulates No production in macrophages.

Figure 13:
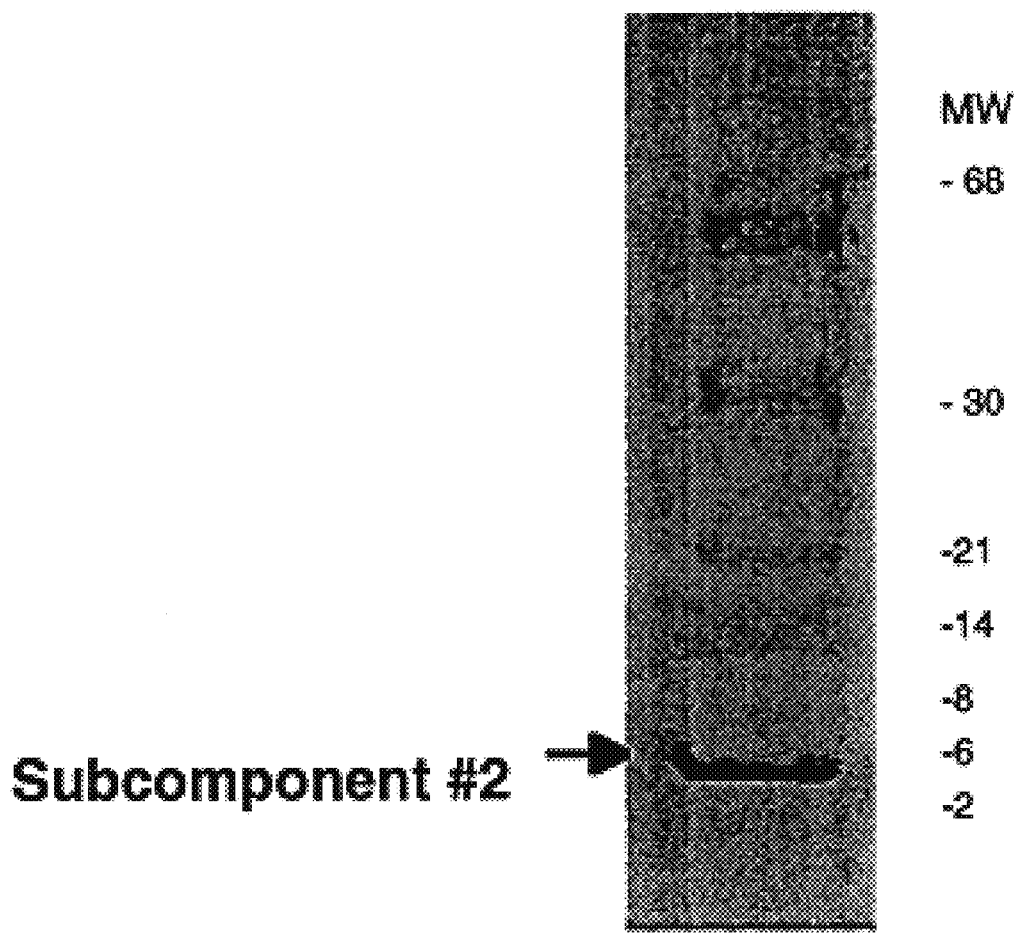
FIG. 13 is a non-reducing SDS acrylamide gel after further protein purification by reverse phase chromatography. Following this step, a prominent 3–8 kD band is observed, NRFSCI$_{3-8}$. Stained with amido black, this band is fully active when eluted from gels and tested in vitro and in vivo.

NRF has been purified from medium conditioned by cells of the mouse hippocampal cell line (HN cells) that are treated with hydrogen peroxide. Small amounts of this peptide rescue significant numbers of these cells and their processes after oxidative insult. The peptide is purified by ion-exchange, reverse phase chromatography and preparative gel electrophoresis with SDS. It is identified after the electrophoresis step by elution of a fully active protein from a gel band with an apparent molecular weight of 3–6 kD and is referred to herein as $NRFSCI_{3-6}$. In appears with other bands of 14, 17, 21, 30 and 65 kD which may represent aggregates or partially unfolded versions of the peptide. See FIG. 13. All of these except the 65 kD band disappear or are greatly reduced when the eluted protein band is rerun under reducing conditions suggesting that the protein is tightly folded in its native form. The N-terminal sequence of the 3–6 kD band or its aggregates reveals a novel mammalian peptide with homology to surface proteins of bacteria as well as plant storage proteins such as lectins. This sequence is the same as that set forth in Sequence I.D. No. 3.

Figure 14:
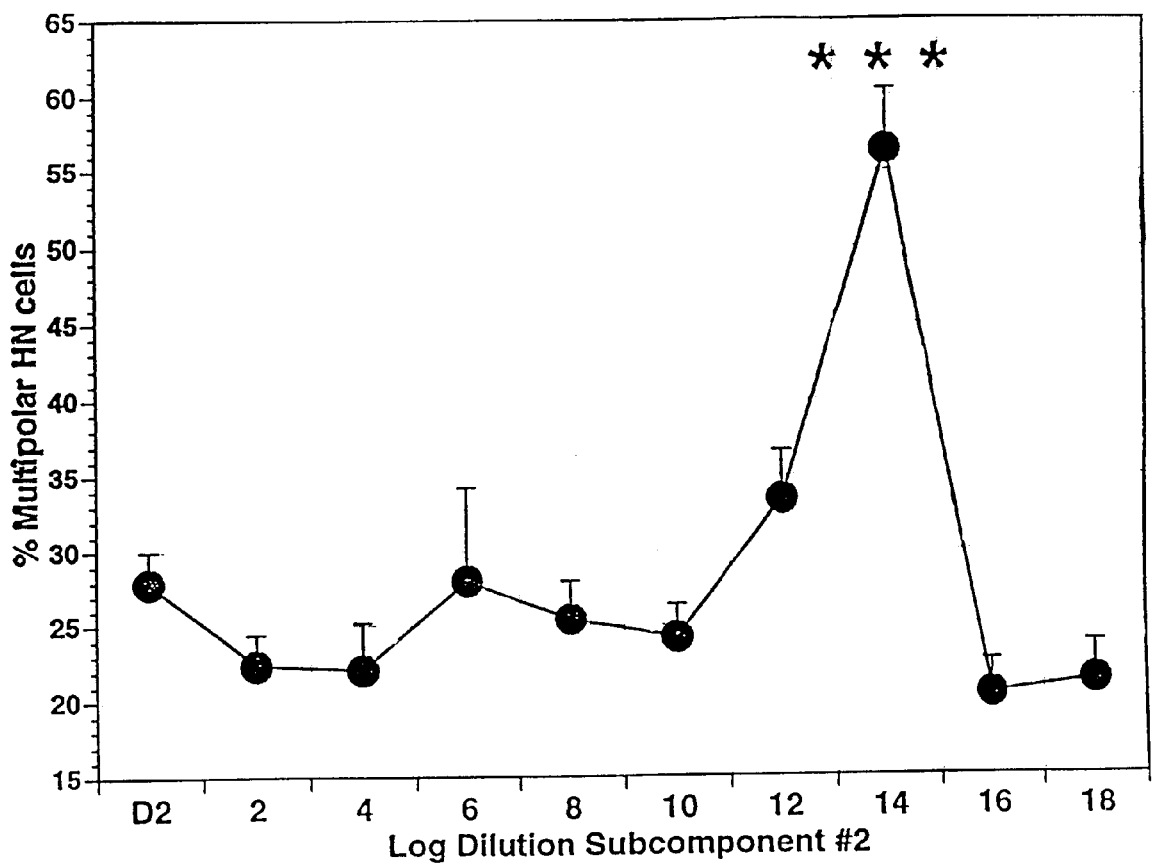
FIG. 14 is a graph showing survival of multipolar HN cells grown on collagen and exposed to 0.03% $H_2O_2$ for 15 minutes followed by two additional medium changes 20 minutes apart. Cell with multiple interconnecting processes were counted after actin immunostaining and compared to control.
Figure 15:
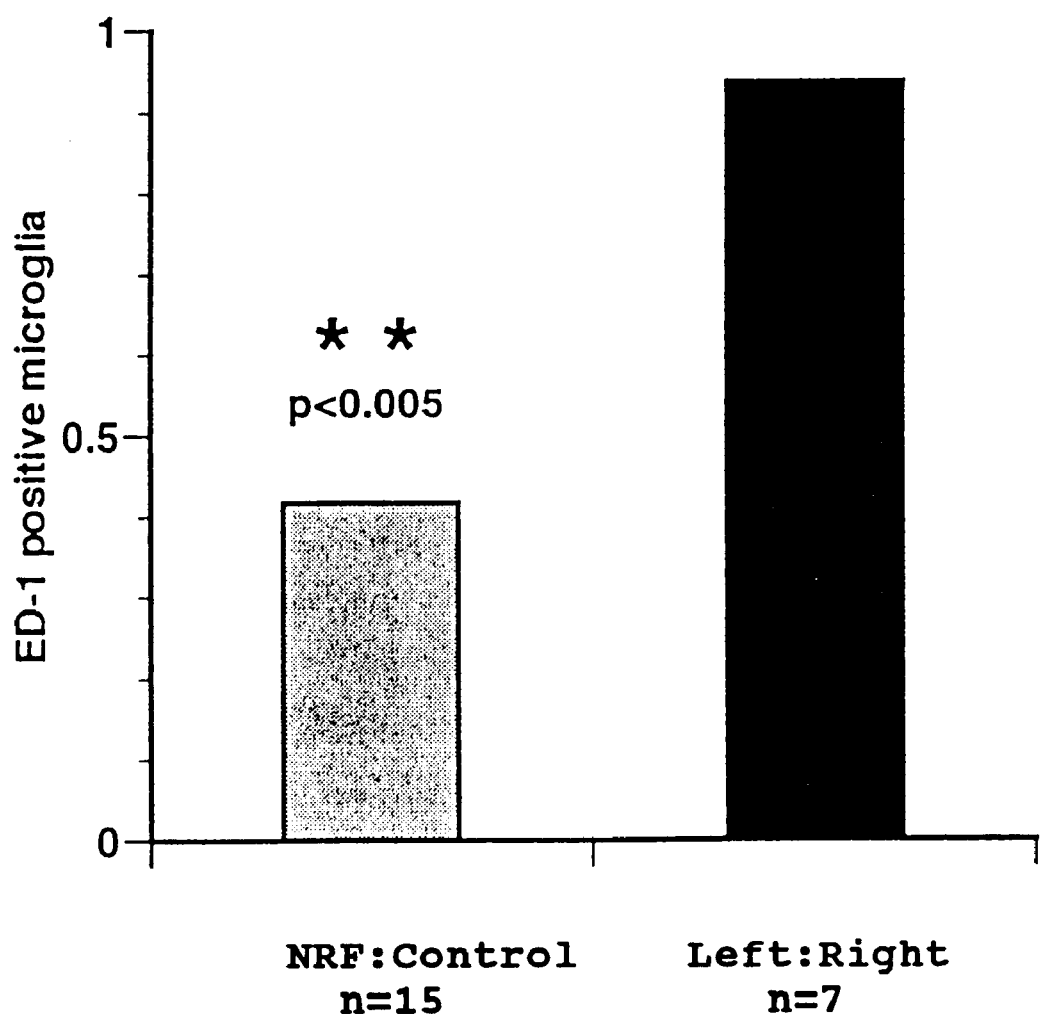
FIG. 15 is a graph illustrating microglia inhibition near the margins and in subjacent white matter of lagre bilateral cerebral cortex lesions in cortical area 2. One side received a gel foam implant containing NRFSCI$_{3-8}$. Counts are of ED-1 positive cells with a ramified positively stained processes characteristic reactive microglia. The side treated with NRFSCI$_{3-8}$ has a 50% reduction in immunostained microglia.
Figure 16:
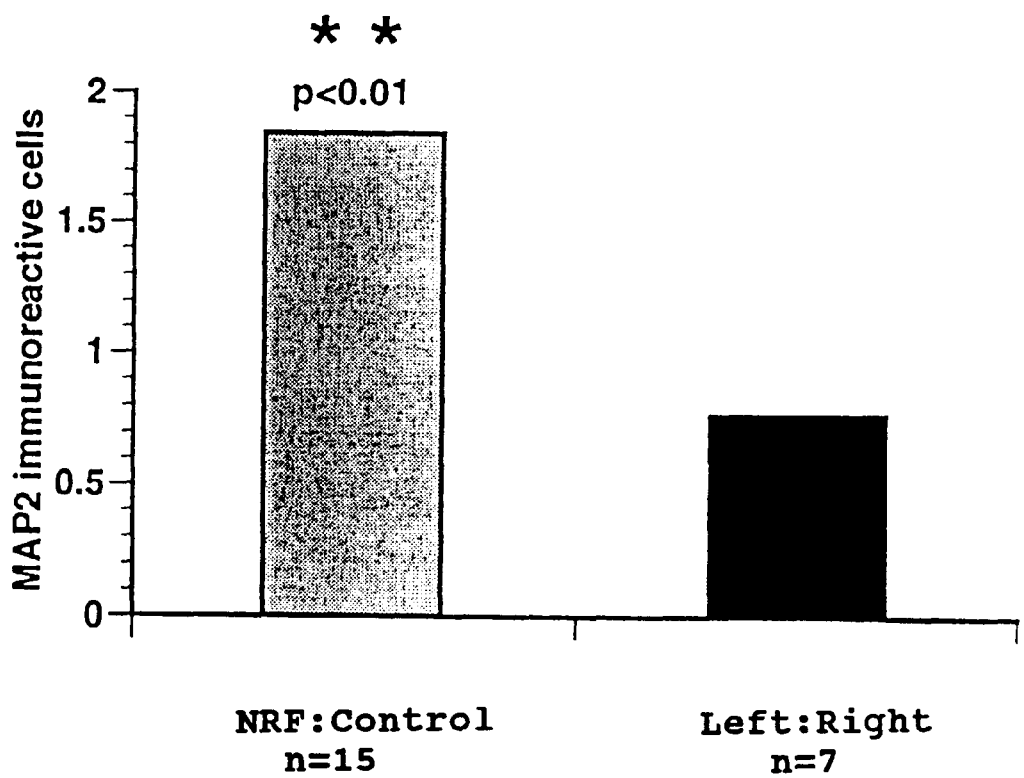
FIG. 16 is a graph showing the density of MAP2 immunostained pyramidal neurons in layers 3 and 5 lateral to bilateral cerebral cortex lesions in area 2. MAP2 is widely used as an early indicator of neuronal deterioration. The regions examined are above the rhinal fissure and include surviving area 2, 40, 14. The treated side of the cortex has a 2-fold increase in immunopositive neurons. Medial to the lesion, only layer 3 is significantly increased on the NRFSCI$_{3-8}$ treated side.

Addition of the diluted $NRFSCI_{3-6}$ peptide to confluent HN cells increases both Ig immunostaining and surface clustering of HN cells, the dilution of 1 ml gel eluent between $10^{12}$ and $10^{14}$ being the most efficacious. Similar dilutions rescue HN cells and their processes which have been established on collagen substrates that have been treated with 0.01–0.5% $H_2O_2$ and subjected to two medium changes. See FIG. 14. The effect is seen as quickly as 60 minutes and after 24 hours. In most experiments, a fall off of activity is observed at high concentrations. This effect can be overcome by pre-incubation of the peptide with N-acetyl neuraminic acid or whole mouse IgG. Similar concentrations of these reagents eliminate activity at effective dilutions of the peptide suggesting that a concentration dependent peptide-sialo-Ig linkage is required for survival promoting activity. The results suggest that the $NRFSCI_{3-6}$ peptide is a lectin-like molecule that may be part of the natural defenses of the HN cell line and may represent a conserved species that operates at the surface of a variety of cell types.

Recent data obtained on the novel neuron rescuing factor $NRFSCI_{3-6}$ indicate that microglia do contribute to the destructive effects of lesions (See FIGS. 13–16. One of the striking effects of this molecule in vivo is its ability to inhibit microglia reactivity after cerebral cortex lesions. See FIG. 15. This is accompanied by a marked reduction in the degradation of neurons in the treated hemispheres. See FIG. 16. Previous work by others on a similar factor suggests that these effects on microglia may be due to inactivation and/or binding of factors with direct effects on monocyte-derived cells, e.g, interferons/MIF (see below).

$NRFSCI_{3-6}$ is closely associated with glycosylated segments of some globular proteins like albumin and Ig and will bind specifically sialidated Ig sequences on the cell surface. During purification, it routinely co-purifies with albumin and Ig sequences. $NRFSCI_{3-6}$ aggregates these cell surface components by a well known process called patching. Interestingly, both the surface patching and in vitro cytoprotective effects are concentration dependent at roughly the same dilutions. N-terminal sequencing of $NRFSCI_{3-6}$ (30AA) shows homology to bacterial wall proteins (which are notorious for binding with surface globular proteins in host animals, often through glycan intermediates), wheat germ glutenin (sialic acid binding lectin) and photochain participants which may transfer electrons to enzymes responsible for regeneration of free radical scavengers. Thus, the sequence information obtained thus far is very consistent with the biological properties of this peptide. The proteins or peptides demonstrating homology to the NRF-SCI peptide of the invention are listed below:

NRFSCI-Amino Acid Sequence and Homologies

N-terminal Sequence: X-Asp-Pro-Glu-Ala$^5$ Ala-Ser-Ala-Pro-Gly$^{10}$ Ser-Gly-Asn-Pro-Cys$^{15}$ His-Glu-Ala-Ser-Ala$^{20}$ Ala-Gln-X-Glu-Asn$^{25}$ Ala-Gly-Glu-Asp-Pro$^{30}$ (See SEQ ID No: 3)

Amino acids shown in bold have been detected in mouse (4 kD, 17–20 kD aggregate) and human (17–20 kD aggregate), amino acids not shown in bold have been identified in the human 17–20 kD aggregate.
Bacterial wall antigens
PREABSORBING ANTIGEN
(*Streptococcus aureus*)
13AA fragment
NRF/CPP: AA 2–14; identities=10/12 (83%), positives=11/12 (91%)
MAJOR MEROZOITE SURFACE ANTIGEN PRECURSOR
(*Plasmodium yoelli*)
AA 977–998 length=1772
NRF/CPP: AA 5–26; 11/22 (50%) 4/22 positives (63%)
Plant Lectin (Storage)
LATE EMBRYOGENESIS ABUNDANT PROTEIN
Hirsutum(cotton)
AA 91–109 length=145
NRF/CPP: AA 12–30 identities=6/19 (31%) positives=9/19 (47%)
WHEAT GLUTENIN HIGH MW SUBUNIT PRECURSOR Triticumaestivum
AA 530–557 length-838
NRF/CPP: AA 3–30 identities=8/28 (28%) positives=14/28 (50%)
Growth related
TRANSFORMING PROTEIN (N-MYC)
*Rattus Norvegicus*
AA-230–256 length=462
NRF/CPP: AA 3–29 identities=11/27 (40%) positives=13/27 (48%)

$NRFSCI_{3-6}$ has features which are also similar to sarcolectin, an alpha/beta interferon antagonist that also binds migration inhibitory factor (MIF), another interferon-like cytokine (Chany, 1987, J. Interferon Res. 7:569–574; Chany-Fournier, et al., 1978, Proc. Natl. Acad. Sci. 75:2333–2337; Chany-Fournier et al., 1990, J. Cell Physiol. 145:173–180; Zeng et al., 1993, Arch. Biochem. Biophys. 303:74–80; Zeng, et al., 1994, Biol. Chem. Hoppe-Seyler 375:393–399; Zeng et al., 1994, Biochem. Biophys. Res. Comm. 200:89–94). This suggestion is based on sialic acid binding and co-dependence, chromatographic and electrophoretic behavior, and very close association with serum proteins. In fact, previous investigations into the chemical makeup of sarcolectin (purified by anion exchange with an occasional but not routine preparative electrophoresis step), led to the conclusion in 1994 that sarcolectin was an unusual fragment of serum albumin.

The purification procedure described herein includes relatively strong acid extraction following anion exchange (150 mM HCl), then cation exchange at low pH, reverse phase chromatography, and preparative electrophoresis. This approach has facilitated the identification of a highly charged non-albumin/Ig low molecular weight (apparent 3–6 kD) albumin/Ig binding species that is largely responsible for the lectin-like properties of sarcolectin. The peptide stains irregularly with some of the conventional protein dyes and is often negatively stained with silver reagent due to its strong negative charge. It stains more typically with these anionic dyes if in high concentration or aggregated. In addition, concentrations of $NRFSCI_{3-6}$ are difficult to estimate because of: 1) relatively low reactivity to standard protein assay reagents (e.g. BCA) and 2) absent or inaccessible aromatic amino acids resulting in low absorbance at 280 nm, which also contributes to the lack of reactivity to assay reagents. Thus, it is not surprising that this molecule could be overlooked or mistaken for a larger, more accessible protein, to which it binds.

Interferons are classified as alpha, beta or gamma and comprise a large molecular family of peptides that play a critical role in mobilizing and coordinating local inflammatory processes. They have multiple specific actions and are produced during inflammatory infectious stimulation and presumably under conditions of widespread cellular destruction. The effects of IFN-α and β on macrophages and microglia is to amplify the immune response by stimulation of inflammatory cytokines including IL-1 and IL-6, and tumor necrosis factor-α. These factors have a variety of additional actions on other immune system cells, but the net effect of the interferons is to increase the cytotoxic capacity of macrophages against tumor cells, and participate in the lysis of intracellular organisms and in the lysis of bacteria. It is therefore not surprising that stimulation of microglia, macrophages, and perhaps interferons themselves as part of the natural phagocytic sequellae to neuronal degeneration might contribute to the degradation of nerve cells and their processes.

The potential binding of $NRFSCI_{3-6}$ to MIF is very important functionally. MIF is also a pro-inflammatory cytokine that affects a number of macrophage functions (Bloom and Bennett, 1966; Nathan et al, 1973; Weiser, 1989; Pozzi and Weiser, 1992; Cunha, et al 1993). The ability to stimulate macrophage killing of parasites and tumor cells may be particularly relevant. In fact, rMIF induces nitric oxide production in murine macrophages (Cunha, et al, 1993), one of the agents implicated in the toxic effects of microglia/BMOs following CNS lesions. One aspect of the invention is the determination of NO synthase levels in macrophages, which parallel NO production, in response to a variety of stimuli including MIF, NRF and subcomponents thereof and MIF bound to NRFSCI.

Figure 12:
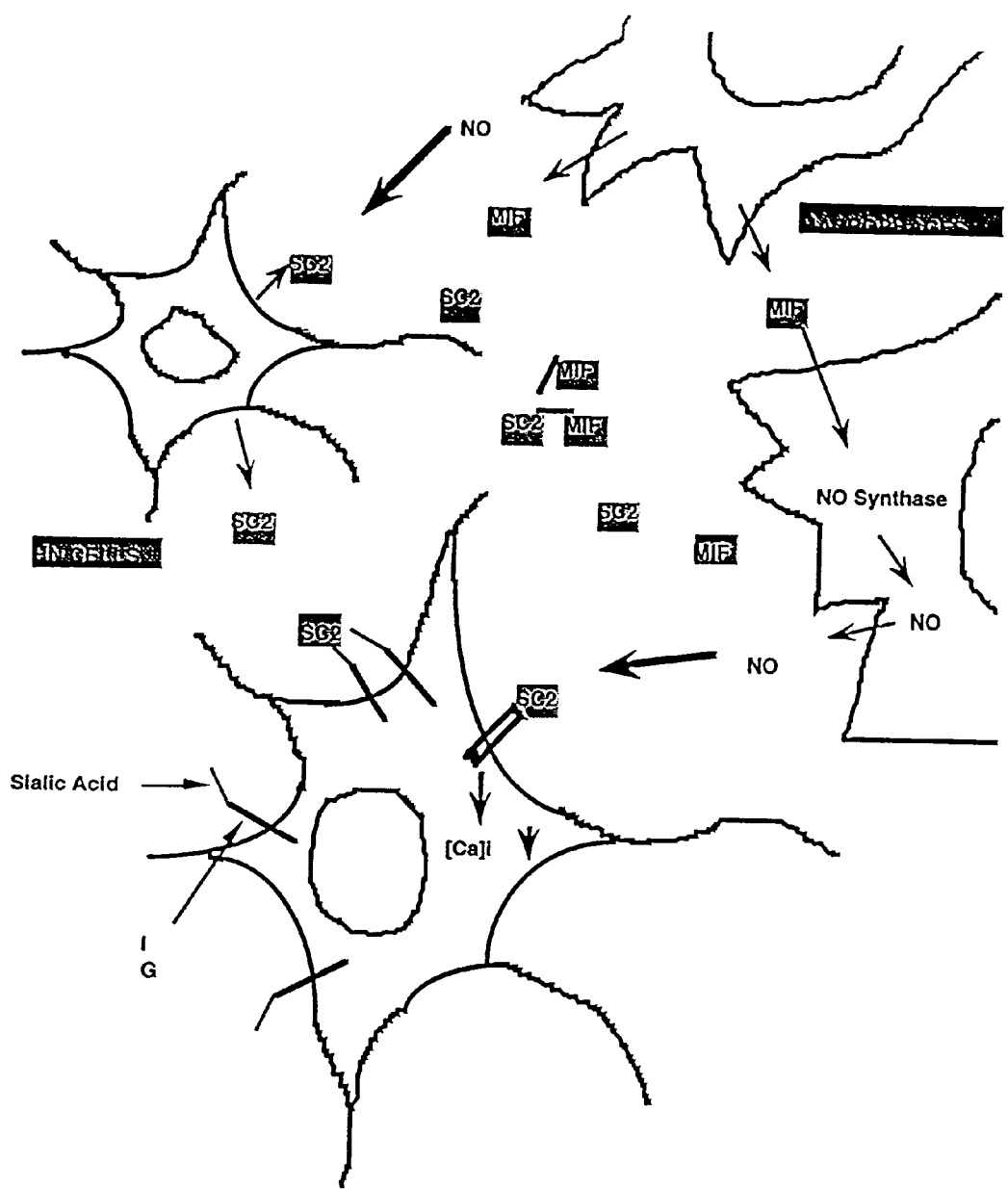
FIG. 12 is a schematic and simplified illustration of how HN cells might in theory defend themselves against macrophages and thereby produce agents like NRFSCI$_{3-8}$ which is presumably beneficial in situations of macrophage toxicity (e.g., CNS lesions). Oxidants including NO stimulate the release of NRF/CPP. As part of the toxic cascade, macrophages release MIF (Calandra, et al., J. Exp. Med. 179:1895–1902, 1994), which in turn stimulates NO production in adjacent macrophages. As part of the defensive cascade, NRFSCI$_{3-8}$ binds to MIF making it unavailable. It also cross links surface Ig via sialo conjugates which ultimately reduces intracellular calcium.

The significance of this work to nervous system recovery lies in the observation that a previously unrecognized and diffusible agent may be available to manipulate the invasive and toxic activity of monocyte-derived cells after lesions in order to promote return of function. In addition, other applications of NRF or its subcomponents may be efficacious in the treatment of neoplastic disease. NRF production by cell lines serve as a two-fold defensive system for continued survival of the line: 1) Lectin-like cross linking activity at the surface to limit stimulus induced accumulation of toxic levels of intracellular Ca (see for example Sehgal, et al., 1993, J. Immunol. 150:4571–4580), and 2) disabling of phagocytic cells to limit their toxic secretions, as shown in FIG. 12. Thus, in some situations, disarming rapidly growing cells by inhibiting NRF activity may prove to be beneficial in the clinical setting.

EXAMPLE 13

As discussed in previous examples and set forth in sequence I.D. No. 3, the amino terminus of NRFSCI has been sequenced. It is an object of the present invention to clone NRFSCI peptide to provide an abundant source of the protein for further biochemical and molecular analysis. The purified protein may also be used to advantage to facilitate neuronal healing following insult. The amino terminal sequence is set forth below (Seq. I.D. No. 3).

$Xaa_1$-Asp-Pro-Glu-Ala-Ala-Ser-Ala-Pro-Gly-Ser-Gly-Asn-Pro-$Xaa_2$-His-Glu-Ala-Ser-Ala-Ala-Gln-$Xaa_3$-Glu-Asn-Ala-Gly-$Xaa_4$-Asp-Pro.

In Sequence I.D. No. 3, $Xaa_2$ is probably Cys and $Xaa_4$ is probably Glu.

The following oligonucleotide probes would be utilized to probe cDNA libraries to facilitate isolation of a clone encoding the NRFSCI protein of the invention. Depending on the abundance of NRFSCI mRNA expressed in a given cell type, oligonucleotides between 30 and 40 bases in length consisting of portions of the sequences listed below should also facilitate isolating clones encoding NRFSCI. Additionally, sequences complementary to those listed below may be used to advantage to isolate NRFSCI encoding clones. Where bases are listed as N, inosine may be substituted in the sequence.

Sequence I.D. No. 4:
5'-NNNCTGGGGC TGCGACGATC GCGAGGGCCG TCGCCGTTGG
GGNNNGTGCT CCGATCGCGA CGAGTCNNNC TCTTGCGACC GNNNCTG-3'

Sequence I.D. No. 5:
5'-NNNCTAGGAC TTCGGCGGAG GCGGGGACCT AGGCCTTTAG
GANNNGTACT TCGGAGGCGG CGGCTTNNNC TTTTACGGCC TNNNCTA-3'

Sequence I.D. No. 6:
5'-NNNCTGGGTC TCCGTCGTAG ACGTGGTCCC AGACCCTTAG

GTNNNGTGCT CCGTAGACGT CGTGTCNNNC TCT-
TGCGTCC CNNNCTG-3'
Sequence I.D. No. 7:
5'-NNNCTGGGGC TCCGGCGGTC GCGGGGGCCG
TCGCCGTTGG
GGNNNGTACT TCGGTCGCGG CGGGTTNNNC TTT-
TACGGCC GNNNCTA-3'
Sequence I.D. No. 8:
5'-NNNCTGGGGC TGCGACGATC GCGAGGGCCG
TCGCCGTTGG
GGACGGTGCT CCGATCGCGA CGAGTCNNNC TCT-
TGCGACC GCTCCTG-3'
Sequence I.D. No. 9:
5'-NNNCTAGGCC TTCGCCGCAG TCGCGGCCCA
AGACCATTAG
GCACGCTACT TCGCAGACGC CGCGTTNNNC TTT-
TACGCCC ACTCCTA-3' cDNA libraries are both commercially available and readily prepared by one of skill in the art of recombinant DNA technology. Procedures for preparing a cDNA library are set forth in *Current Protocols in Molecular Biology*, (1995) J. Wiley and Sons, Inc. Following synthesis, the oligonucleotides described above may be labeled with a detectable label such as a $^{32}P$, fluorescent or a chemiluminescent label and used to probe the cDNA library. Positive clones would then be isolated and the hybridizing DNA isolated, further characterized and sequenced. Such procedures should facilitate cloning of a cDNA molecule encoding NRFSCI. The cDNA clone so obtained may then be used to probe a human genomic library and the gene encoding the NRFSCI isolated.

In the last decade, it has become evident that strategies designed to repair damaged nervous tissue will depend on an understanding of mechanisms operative in both the hematopoietic and immune systems. NRF and its subcomponents described herein protect nerve cells destined to die after damage to the cerebral cortex, and at the same time inhibit the reactivity of microglia, a monocyte-derived phagocytic cell in the nervous system. NRF of the invention has also been shown to aggregate or "patch" sialo-Ig conjugates on the surface of the HN cells, and in addition, protect these cells and their processes from degradation following oxidative insult.

EXAMPLE 14

The availablility of the amino acid sequence of NRF has facilitated the chemical synthesis of this protein. A synthetic peptide, having the sequence of Sequence I.D. No. 10 was chemically synthesized and biochemically characterized.
Sequence I.D. No. 10:
Tyr-Asp-Pro-Glu-Ala-Ala-Ser-Ala-Pro-Gly-Ser-Gly-
Asn-Pro-Cys-His-Glu-Ala-Ser-Ser-Ala-Gln-Cys-Glu-
Asn-Ala-Gly-Glu-Asp-Pro.

Figure 17A:
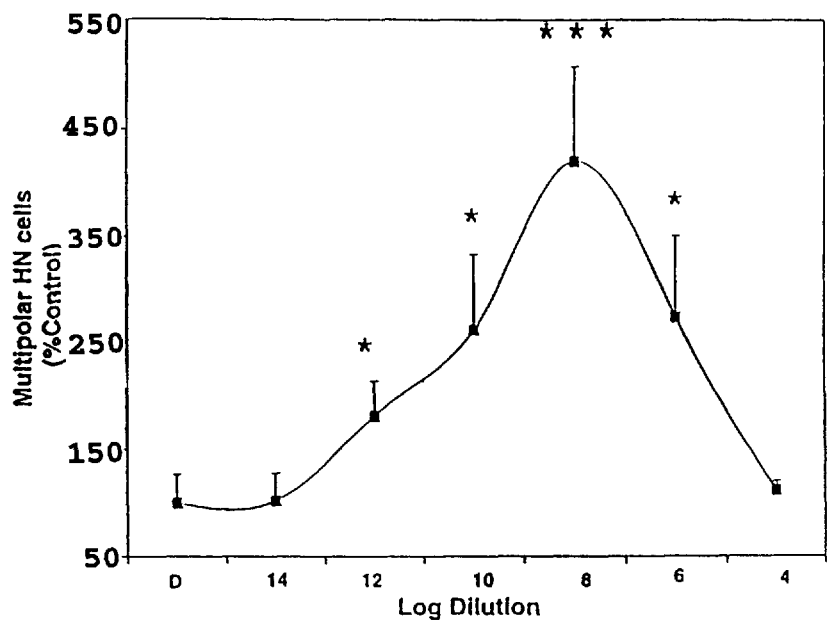
FIGS. 17A and 17B are a pair of graphs showing the effects of native NRFSCI$_{3-8}$ and synthetic NRF on the survival of $H_2O_2$ treated HN cells.
Figure 17B:
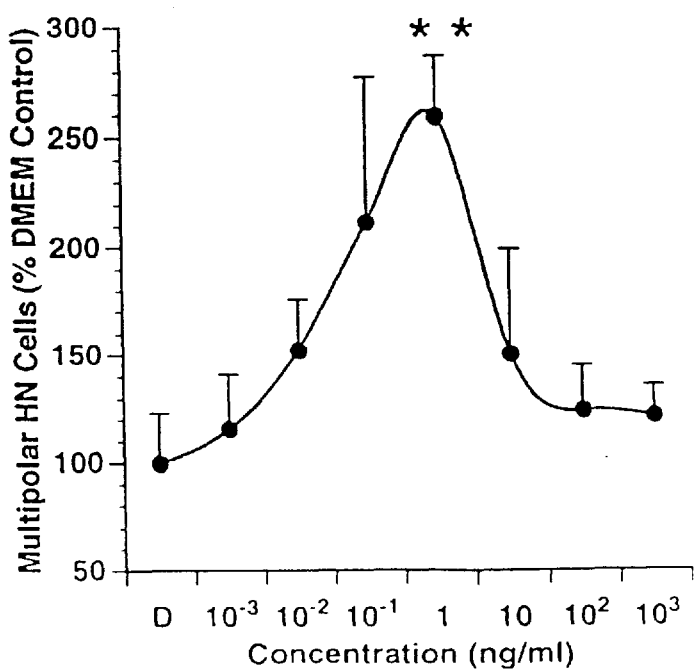

As shown in FIG. 17, the synthetic peptide is just as effective in stimulating the survival of HN cells as is NRF purified from $H_2O_2$ treated cells. A scrambled synthetic peptide did not exhibit any growth stimulating effects on these cells (data not shown).

Figure 18:
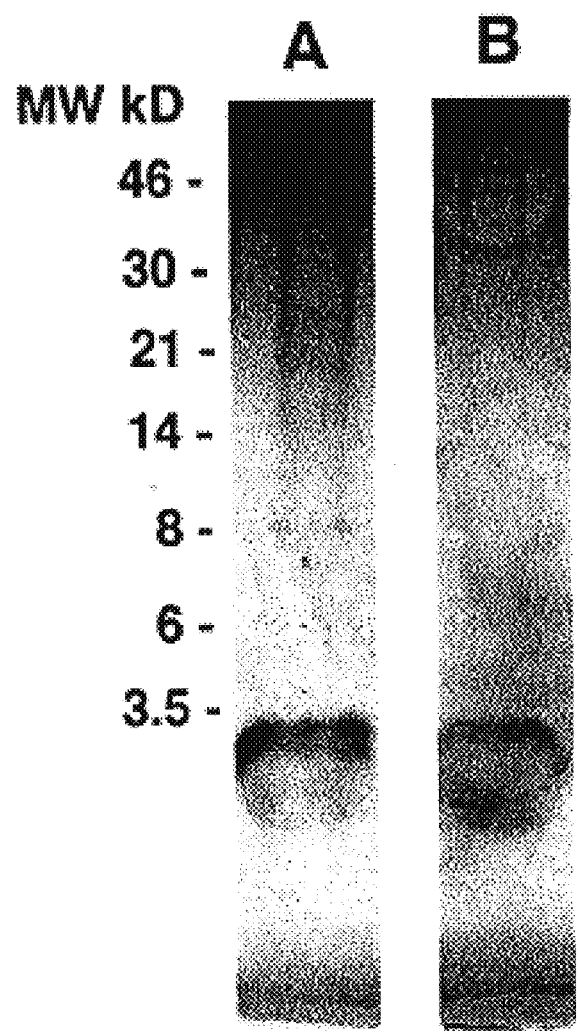
FIG. 18 is a polyacrylamide gel showing the similar migration and staining pattern exhibited by the synthetic NRF peptide and native NRFSCI$_{3-8}$.

The synthetic NRF peptide and native NRF purified from retinoblastoma cells were subjected to comparative electrophoresis and protein staining. The results are shown in FIG. 18. The data indicate that the synthetic peptide migrates with authentic $NRF_{3-8}$ purified from these cells and exhibits identical staining characteristics. The synthetic peptide may be able to form multimeric complexes giving rise to the higher molecular weight complexes described in the previous examples. Inasmuch as the synthetic NRF peptide mimics native NRF in promoting the survival of HN cells and biochemical characteristics, it appears that the amino acids of NRFSCI corresponding to the synthetic NRF peptide are sufficient to promote neuron survival in vivo and in vitro.

The present invention is not limited to the embodiments specifically described above, but is capable of variation and modification without departure from the scope of the appended claims.

---

What is claimed is:

1. A purified, secretable, acidic neuron regulatory factor (NRF) complex isolated from rat neonatal cerebral cortex, or from human retinoblastoma cells, wherein said NRF complex does not comprise NGF, CNTF, bFGF, or aFGF, yet consists of a complex of polypeptides exhibiting an apparent molecular weight of between about 200 kDa and 220 kDa as determined by SDS-polyacrylamide gel electrophoresis under non-reducing conditions, wherein said NRF complex increases survival of cultured embryonic posterolateral thalamic neurons, hippocampal neurons and dorsal lateral geniculate nucleus neurons, and wherein said NRF complex activity is inhibited by 5 mM glycine.

2. The neuron regulatory factor complex of claim 1, having as a component a cytoprotective protein, Neuron Regulatory Factor, subcomponent I (NRFSCI) consisting of SEQ ID NO: 3.

3. A purified Neuron Regulatory Factor, subcomponent I (NRFSCI) cytoprotective protein comprising at least one polypeptide of 2.5 kDa when treated with SDS and DTT without boiling, or 14–21 kDa when treated with SDS and DTT with boiling said at least one polypeptide comprising a sequence selected from the group consisting of SEQ ID NO:3 and SEQ ID NO: 10, wherein said NRFSCI cytoprotective protein increases survival of cultured retinoblastoma cells in vitro.

4. A synthetic neuron regulatory peptide comprising SEQ ID NO: 10 wherein said peptide stimulates survival of hippocampal neurons.

5. A synthetic neuron regulatory peptide consisting of the sequence depicted as SEQ ID NO: 10.

6. An isolated polypeptide produced by the expression of an isolated and purified nucleic acid molecule, said nucleic acid molecule being selected from the group consisting of DNA and RNA, which encodes a polypeptide consisting of amino acid sequence selected from the group consisting of SEQ ID NO: 3 and SEQ ID NO: 10.

7. A composition comprising a NRFSCI protein amino acid sequence depicted as SEQ ID NO: 3, and a pharmaceutically acceptable carrier wherein said NRFSCI protein promotes thalamic neuron survival.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 21 amino acids
      (B) TYPE: amino acid
      (D) TOPOLOGY: linear (ii) MOLECULE TYPE: peptide (xi) SEQUENCE DESCRIPTION: SEQ ID NO: 1:

Asp Leu Tyr Ala Asn Thr Val Leu Ser Gly Gly Thr Thr Met Tyr
1               5                   10                  15

Pro Gly Ile Ala Asp Arg
            20

(2) INFORMATION FOR SEQ ID NO: 2:

(i) SEQUENCE CHARACTERISTICS:
      (A) LENGTH: 15 amino acids (B) TYPE: amino acid
        (D) TOPOLOGY: linear (ii) MOLECULE TYPE: peptide (xi) SEQUENCE DESCRIPTION: SEQ ID NO: 2:

Tyr Pro Ile Glu His Gly Ile Val Thr Asn Trp Asp Asp Met Glu
1               5                   10                  15

(2) INFORMATION FOR SEQ ID NO: 3:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 3:

Xaa Asp Pro Glu Ala Ala Ser Ala Pro Gly Ser Gly Asn Pro Xaa
1               5                   10                  15

His Glu Ala Ser Ala Ala Gln Xaa Glu Asn Ala Gly Xaa Asp Pro
                20                  25                  30

(2) INFORMATION FOR SEQ ID NO: 4:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 4:

NNNCTGGGGC TGCGACGATC GCGAGGGCCG TCGCCGTTGG GGNNNGTGCT                 50

CCGATCGCGA CGAGTCNNNC TCTTGCGACC GNNNCTG                              87

(2) INFORMATION FOR SEQ ID NO: 5:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 5:

NNNCTAGGAC TTCGGCGGAG GCGGGGACCT AGGCCTTTAG GANNNGTACT                 50

TCGGAGGCGG CGGCTTNNNC TTTTACGGCC TNNNCTA                              87

(2) INFORMATION FOR SEQ ID NO: 6:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 6:

NNNCTGGGTC TCCGTCGTAG ACGTGGTCCC AGACCCTTAG GTNNNGTGCT            50

CCGTAGACGT CGTGTCNNNC TCTTGCGTCC CNNNCTG                          87

(2) INFORMATION FOR SEQ ID NO: 7:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 7:

NNNCTGGGGC TCCGGCGGTC GCGGGGGCCG TCGCCGTTGG GGNNNGTACT            50

TCGGTCGCGG CGGGTTNNNC TTTTACGGCC GNNNCTA                          87

(2) INFORMATION FOR SEQ ID NO: 8:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 8:

NNNCTGGGGC TGCGACGATC GCGAGGGCCG TCGCCGTTGG GGACGGTGCT            50

CCGATCGCGA CGAGTCNNNC TCTTGCGACC GCTCCTG                          87

(2) INFORMATION FOR SEQ ID NO: 9:

(i) SEQUENCE CHARACTERISTICS:
        (A) LENGTH: 87 bases
        (B) TYPE: nucleic acid
        (C) STRANDEDNESS: single
        (D) TOPOLOGY: linear (ii) MOLECULE TYPE: DNA (iii) HYPOTHETICAL: No (iv) ANTI-SENSE: No (xi) SEQUENCE DESCRIPTION: SEQ ID NO: 9:

NNNCTAGGCC TTCGCCGCAG TCGCGGCCCA AGACCATTAG GCACGCTACT            50

TCGCAGACGC CGCGTTNNNC TTTTACGCCC ACTCCTA                          87

(2) INFORMATION FOR SEQ ID NO: 10:

(i) SEQUENCE CHARACTERISTICS:

```
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 10:

Tyr Asp Pro Glu Ala Ala Ser Ala Pro Gly Ser Gly Asn Pro Cys
1               5                   10                  15

His Glu Ala Ser Ser Ala Gln Cys Glu Asn Ala Gly Glu Asp Pro
                20                  25                  30
```